United States Patent [19]
Klimkowski et al.

[11] Patent Number: 5,811,402
[45] Date of Patent: Sep. 22, 1998

[54] ANTITHROMBOTIC DIAMIDES

[75] Inventors: Valentine Joseph Klimkowski, Carmel; Michael Robert Wiley, Indianapolis, both of Ind.

[73] Assignee: Eli Lilly and Company, Indianapolis, Ind.

[21] Appl. No.: 818,463

[22] Filed: Mar. 17, 1997

Related U.S. Application Data

[60] Provisional application No. 60/013,865, Mar. 22, 1996.
[51] Int. Cl.⁶ .................... A61K 38/05; C07D 401/12; C07D 403/12
[52] U.S. Cl. .................... 514/19; 514/326; 514/397; 548/312.1; 548/314.7; 546/210
[58] Field of Search .................... 548/312.1, 314.7; 546/210; 514/19, 326, 397

[56] References Cited

U.S. PATENT DOCUMENTS

| | | | |
|---|---|---|---|
| 4,346,078 | 8/1982 | Bajusz et al. | 424/177 |
| 5,453,430 | 9/1995 | Lassalle et al. | 514/312 |
| 5,510,369 | 4/1996 | Lumma et al. | 514/422 |
| 5,523,308 | 6/1996 | Costanzo et al. | 514/317 |
| 5,561,146 | 10/1996 | Kim et al. | 514/326 |
| 5,583,146 | 12/1996 | Kimball et al. | 514/326 |
| 5,599,793 | 2/1997 | Chirgadze et al. | 514/19 X |
| 5,602,101 | 2/1997 | Schacht et al. | 514/19 X |
| 5,614,499 | 3/1997 | Bylund et al. | 514/19 |
| 5,629,324 | 5/1997 | Vacca et al. | 514/326 X |
| 5,639,739 | 6/1997 | Dominguez et al. | 514/64 |

FOREIGN PATENT DOCUMENTS

| | | |
|---|---|---|
| 16380/95 | 10/1995 | Australia . |
| 21801/95 | 1/1996 | Australia . |
| 601 459 | 6/1994 | European Pat. Off. . |
| 648 780 | 4/1995 | European Pat. Off. . |
| 669 317 | 8/1995 | European Pat. Off. . |
| 677531 | 10/1995 | European Pat. Off. . |
| 686 642 | 12/1995 | European Pat. Off. . |
| 195 48 797 | 7/1997 | Germany . |
| 93/11152 | 6/1993 | WIPO . |
| 94/29336 | 12/1994 | WIPO . |
| 95/23609 | 9/1995 | WIPO . |
| 95/35309 | 12/1995 | WIPO . |
| 96/03374 | 2/1996 | WIPO . |

OTHER PUBLICATIONS

Bajusz, S., "Interaction of Trypsin–like Enzymes with Small Inhibitors," *Symposia Biologica Hungarica*, 25, 277–298, (1984).

Scarborough, R. M., "Anticoagulant Strategies Targeting Thrombin and Factor Xa," *Annual Reports in Medical Chemistry*, 30, 71–80, (1995).

Edmunds, J. J., et al., "Thrombin and Factor Xa Inhibition," *Annual Reports in Medical Chemistry*, 31, 51–60 (1996).

Misra, Raj N., et al., *Bioorg. & Med. Chem. Letters*, 4, 2165–2170, (1994).

Dominguez, C., et al., *Bioorg. & Med. Chem. Letters*, 7, 79–84, (1997).

*Primary Examiner*—Fiona T. Powers
*Attorney, Agent, or Firm*—Thomas E. Jackson; David E. Boone

[57] ABSTRACT

This invention relates to a compound of the Formula I

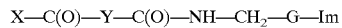

X—C(O)—Y—C(O)—NH—CH$_2$—G—Im       I (wherein X, Y, G and Im have the values defined in the description), or a pharmaceutically acceptable salt thereof, processes and intermediates for the preparation of such a compound or salt, pharmaceutical compositions comprising such a compound or salt and methods of their use as thrombin inhibitors, coagulation inhibitors and agents for the treatment of thromboembolic disorders.

13 Claims, No Drawings

ANTITHROMBOTIC DIAMIDES

This application claims the benefit of U.S. Provisional application Ser. No. 60/013,865, filed Mar. 22, 1996.

This invention relates to thrombin inhibitors which are useful anticoagulants in mammals. In particular it relates to diamides having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the diamides are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation is currently achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80.

Although the heparins and coumarins are effective anticoagulants, no commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

According to the invention there is provided a compound having the Formula I

X—C(O)—Y—C(O)—NH—CH$_2$—G—Im     I wherein

X—C(O)— is D-prolinyl, D-homoprolinyl, $R^m$—(CH$_2$)$_g$—NH—CH$_2$—C(O)—,

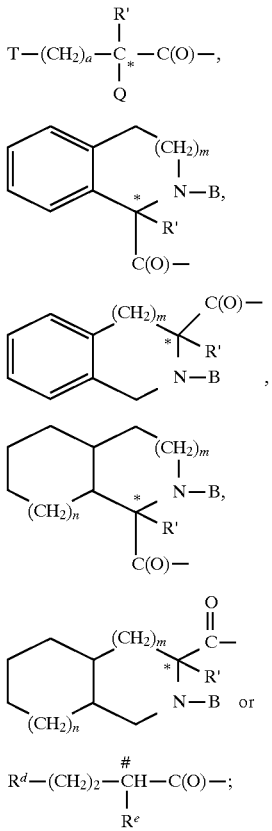

$R^d$—(CH$_2$)$_2$—$\overset{\#}{\underset{R^e}{\text{CH}}}$—C(O)—;

in which $R^d$ is carboxy or methylsulfonyl;

$R^e$ is NHR$^c$, NHCOR$^c$ or NHCOOR$^c$; in which $R^c$ is (C$_1$–C$_{10}$)alkyl, (C$_3$–C$_8$)cycloalkyl or a (C$_3$–C$_8$) cycloalkyl-(C$_1$–C$_6$)alkyl radical of 4–10 carbons;

T is (C$_3$–C$_8$)cycloalkyl, (C$_1$–C$_8$)alkyl,

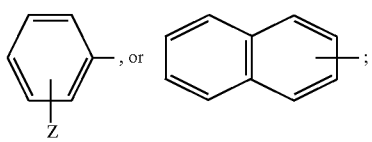

a is 0, 1 or 2; and

Q is —OH, (C$_1$–C$_4$)alkoxy, or —NH—A;

A is hydrogen, (C$_1$–C$_4$)alkyl, R"SO$_2$—, R"OC(O)—, R"C(O)—, R"C(O)— or —(CH$_2$)$_g$—R'";

g is 1, 2, or 3;

B is hydrogen or (C$_1$–C$_4$)alkyl;

R' is hydrogen or (C$_1$–C$_4$)alkyl;

R" is (C$_1$–C$_4$)alkyl, (C$_1$–C$_4$)fluoroalkyl bearing one to five fluoros, —(CH$_2$)$_d$—R'", or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

$R^m$ is —COOR$^b$, —SO$_2$(C$_1$–C$_4$ alkyl), —SO$_3$H, —P(O)(OR$^b$)$_2$ or tetrazol-5-yl;

$R^n$ is —COOR$_b$ or tetrazol-5-yl;

each $R^b$ is independently hydrogen or (C$_1$–C$_4$)alkyl;

d is 1, 2, or 3;

m is 0, 1, or 2;

n is 0, 1, or 2; and

Z is hydrogen, (C$_1$–C$_4$)alkyl, (C$_1$–C$_4$)alkoxy, hydroxy, halo or (C$_1$–C$_4$)alkylsulfonylamino;

—Y—C(O)— is

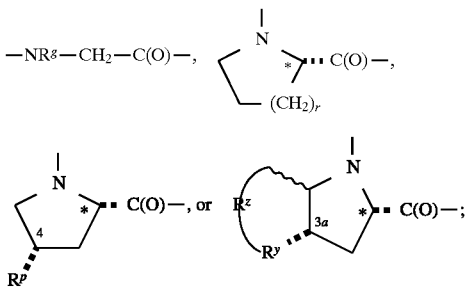

in which $R^g$ is (C$_1$–C$_6$)alkyl, (C$_3$–C$_8$)cycloalkyl, or —(CH$_2$)$_p$—L—(CH$_2$)$_q$—T';

$R^p$ is (C$_1$–C$_6$)alkyl, (C$_3$–C$_8$)cycloalkyl, or —(CH$_2$)$_p$—L—(CH$_2$)$_q$—T';

where p is 0, 1, 2, 3, or 4; L is a bond, —O—, —S—, or —NH—; q is 0, 1, 2 or 3; and T' is (C$_1$–C$_4$)alkyl, (C$_3$–C$_8$)cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

$R^y$ is —CH$_2$-, —O—, —S—, or —NH—; and $R^z$ is a bond or, when taken with $R^y$ and the three adjoining carbon atoms, forms a saturated carbocyclic ring of 5–8 atoms, one atom of which may be —O—, —S—, or —NH—;

r is 0, 1 or 2;

G is —(CH$_2$)$_s$—, where s is 0, 1, 2, 3, or 4, or G is —(CH$_2$)$_t$—CH=CH—, where t is 0, 1, or 2 and the double bond is trans and is bonded to Im; and Im is an imidazol-4-yl group bearing a radical R at the 5-position in which R is hydrogen, a (C$_1$–C$_4$)alkyl radical which may bear a hydroxy substituent, or a (C$_1$–C$_3$)alkoxy-(C$_1$–C$_3$)alkyl radical of 2–4 carbons;

or a pharmaceutically acceptable salt thereof.

In addition to a compound of Formula I, the present invention provides a pharmaceutical composition comprising a compound of Formula I, or a pharmaceutically acceptable salt thereof, in association with a pharmaceutically acceptable carrier, diluent or excipient.

The present invention also provides a method of inhibiting thrombosis in a mammal comprising administering to a mammal in need of treatment, an antithrombotic dose of a compound of Formula I.

The present invention further provides a method of inhibiting thrombin comprising administering to a mammal in need of treatment, a thrombin inhibiting dose of a compound of Formula I.

This invention relates to new inhibitors of thrombin, pharmaceutical compositions containing the compounds as active ingredients, and the use of the compounds as anticoagulants for prophylaxis and treatment of thromboembolic diseases such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

The term "5- or 6-membered aromatic heterocyclic ring" means any 5- or 6-membered ring that will afford a stable structure containing one or two nitrogen atoms; one sulfur atom; one oxygen atom; one nitrogen and one sulfur atom; or one nitrogen and one oxygen atom. The 5-membered ring has two double bonds and the 6-membered ring has three double bonds.

The term "9- or 10-membered fused bicyclic aromatic heterocyclic group" means any bicyclic group in which any of the above 5- or 6-membered rings is ortho fused to a benzene ring or to a 6-membered heterocyclic aromatic ring as defined above in a manner that will afford a stable structure.

It will be appreciated that many of the above heterocycles, as well as the imidazole moiety Im, may exist in tautomeric forms. All such forms are included within the scope of this invention.

Each of the aromatic or heteroaromatic groups listed for the definition of Ar or R'' is independently unsubstituted or substituted with one or two substituents that will afford a stable structure independently selected from halo, hydroxy, (C$_1$–C$_4$)alkyl, (C$_1$–C$_4$)alkoxy, amino, mono(C$_1$–C$_4$ alkyl) amino, di(C$_1$–C$_4$ alkyl)amino, —(CH$_2$)$_j$COOH, mercapto, —S(O)$_h$(C$_1$–C$_4$ alkyl), —NHS(O)$_h$(C$_1$–C$_4$ alkyl), —NHC(O)(C$_1$–C$_4$ alkyl), —S(O)$_h$NH$_2$,—S(O)$_h$NH(C$_1$–C$_4$ alkyl), or —S(O)$_h$N(C$_1$–C$_4$ alkyl)$_2$, h is 0, 1 or 2, and j is 0, 1, 2, 3, or 4.

In the representation of Formula I, the carbonyl functionality of group X—(CO)— is attached to the amine functionality of the —Y—(CO)— group. The carbonyl functionality of —Y—(CO)— is then attached to the amino group drawn in Formula I.

The group

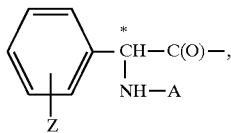

where Z and A are both hydrogen, is referred to at times herein as phenylglycyl and abbreviated Phg. Compounds wherein A is, e.g., methyl, are referred to as the N$^\alpha$-methyl-phenylglycyl group and abbreviated MePhg. Substituted compounds wherein Z is other than hydrogen are referred to by the type and position of the substituent group, e.g., 3'-chlorophenylglycyl or Phg(3-Cl).

The group

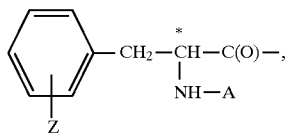

where Z and A are both hydrogen, is referred to at times herein as phenylalanyl and abbreviated Phe. Compounds wherein A is, e.g., methyl, are referred to as the $N^\alpha$-methyl-phenylalanyl group and abbreviated MePhe. Substituted compounds wherein Z is other than hydrogen are referred to by the type and position of the substituent group, e.g., 3'-chlorophenylalanyl or Phe(3-Cl).

The groups

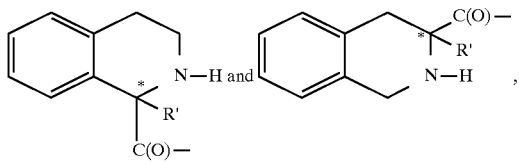

when R' is hydrogen, are referred to at times herein as 1- and 3-tetrahydro-isoquinolinecarbonyl, respectively, and are respectively abbreviated 1-Tiq and 3-Tiq.

The groups

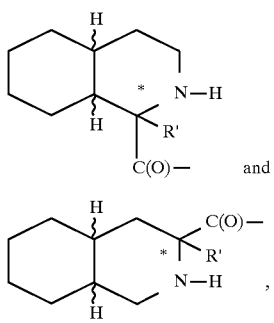

when R' is hydrogen, are referred to at times herein as 1- and 3-perhydro-isoquinolinecarbonyl, respectively, and are respectively abbreviated 1-Piq and 3-Piq. As indicated by the crooked lines, various ring fusion isomers of these substituents exist—this invention contemplates any individual isomer and combinations thereof.

The group

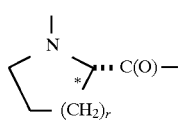

wherein r is 0, 1 or 2 is referred to as azetidine-2-carbonyl, prolinyl, or homoprolinyl, and is abbreviated Azt, Pro or hPro, respectively.

The group

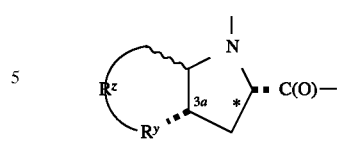

represents a saturated bicyclic system of the 4,5; 5,5; 6,5; 7,5; or 8,5 type. The stereochemistry at 3a is cis to the carbonyl; the other bridgehead bond may be either cis or trans except for the 4,5 and 5,5 systems must be cis at the bridgehead. The definitions of $R^y$ and $R^z$ provide that the variable ring, which includes the three carbon atoms shown, is a saturated carbocyclic system of 4–8 atoms. All of the ring atoms may be carbon, or one of the ring atoms may be a hetero atom selected from —O—, —S—, and —NH—. This definition includes the moiety derived from octahydroindole-2-carboxylic acid, as represented by

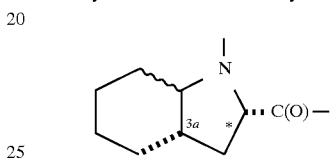

The various cis and trans forms of this moiety are contemplated by this invention. The preferred isomer derived from [2S-(2α,3aβ,7aβ)]-octahydroindole-2-carboxylic acid is abbreviated "Ohi" and is represented by

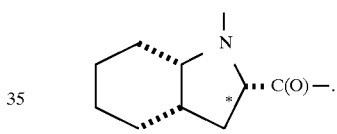

The asterisks in radical Y denote a chiral center that is (L). The asterisk in radical X denotes a chiral center that is (D) or (DL); the # in radical X denotes a chiral center that is (L).

It will be appreciated that certain compounds of Formula I may exist in, and be isolated in, isomeric forms, including tautomeric forms or cis- or trans-isomers, as well as optically active racemic or diastereomeric forms. The present invention encompasses a compound of Formula I in any of the tautomeric forms or as a mixture thereof. It is to be understood that the present invention encompasses a compound of Formula I as a mixture of diastereomers, as well as in the form of an individual diastereomer, and that the present invention encompasses a compound of Formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of Formula I may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a $(C_1-C_4)$alkyl group, a $(C_1-C_6)$ alkyl group, a $(C_1-C_8)$alkyl group or a $(C_1-C_{10})$alkyl group is methyl, ethyl, propyl, isopropyl, butyl, isobutyl or t-butyl.

A particular value for a $(C_1-C_4)$alkoxy group is methoxy, ethoxy, propoxy or isopropoxy. A particular value for a $(C_3-C_8)$cycloalkyl group is cyclopropyl, cyclopentyl or cyclohexyl. A particular value for a $(C_1-C_4)$fluoroalkyl group is trifluoromethyl or 2,2,2-trifluoroethyl. A particular value for aryl is phenyl, naphthyl, furyl, thienyl, pyridyl, indolyl, quinolinyl or isoquinolinyl. A particular value for a $(C_1-C_3)$alkoxy-$(C_1-C_3)$alkyl radical is methoxymethyl, ethoxymethyl, methoxyethyl or ethoxyethyl.

A particular compound of Formula I is one which may be represented by Formula Ia $$X^a-C(O)-Y^a-C(O)-NH-CH_2-G^a-Im^a \quad \text{Ia}$$

wherein $X^a$—C(O)— is D-homoprolinyl, $T^a-(CH_2)_a-\overset{*}{C}H-C(O)-$
$\quad\quad\quad\quad\quad |$
$\quad\quad\quad\quad\quad NH-A^a$ ,

[tetrahydroisoquinoline-1-yl-C(O)— with N—H],

[tetrahydroisoquinoline-3-yl-C(O)— with N—H],

[decahydroisoquinoline-1-yl-C(O)— with N—H, H, H],

[decahydroisoquinoline-1-yl-C(O)— with N—H, H, H] or

[decahydroisoquinoline-3-yl-C(O)— with N—H, H, H];

in which $T^a$ is cyclohexyl or phenyl; a is 0, 1, or 2; and $A^a$ is hydrogen, $(C_1-C_4)$alkyl, $(C_1-C_4$ alkyl)sulfonyl, $(C_1-C_4$ alkyl)oxy-carbonyl, $(C_1-C_4$ alkyl)carbonyl or carboxymethyl;

—$Y^a$—C(O)— is

[pyrrolidinyl/piperidinyl ring with N, $(CH_2)_r$, C(O)—] or

[octahydroindolyl ring with N, C(O)—]

in which r is 0, 1, or 2;

$G^a$ is methylene, ethylene, trimethylene or transvinylidene; and $Im^a$ is an imidazol-4-yl group which may bear a methyl or hydroxymethyl substituent at the 5-position;

or a pharmaceutically acceptable salt thereof.

A preferred compound of Formula Ia is one in which $$X^8-C(O)- \text{ is } T^a-(CH_2)_a-\overset{*}{C}H-C(O)-$$
$$\quad\quad\quad\quad\quad\quad\quad\quad\quad\quad |$$
$$\quad\quad\quad\quad\quad\quad\quad\quad\quad\quad NH-A^a$$

wherein $T^a$ is cyclohexyl or phenyl; a is 1; and $A^a$ is hydrogen, ethylsulfonyl or carboxymethyl;

—$Y^a$—C(O)— is

[pyrrolidinyl ring with N, $(CH_2)_r$, C(O)—] or

[octahydroindolyl ring with N, C(O)—]

in which r is 0, 1, or 2;

$G^a$ is methylene, ethylene or trans-vinylidene; and $Im^a$ is 4-imidazolyl or 5-methylimidazol-4-yl;

or a pharmaceutically acceptable salt thereof.

A more preferred compound of Formula Ia is one in which $$X^8-C(O)- \text{ is } T^a-(CH_2)_a-\overset{*}{C}H-C(O)-$$
$$\quad\quad\quad\quad\quad\quad\quad\quad\quad\quad |$$
$$\quad\quad\quad\quad\quad\quad\quad\quad\quad\quad NH-A^a$$

wherein $T^a$ is cyclohexyl; a is 1; and $A^a$ is hydrogen, ethylsulfonyl or carboxymethyl;

—$Y^a$—C(O)— is

[pyrrolidinyl ring with N, $(CH_2)_r$, C(O)—] or

[octahydroindolyl ring with N, C(O)—]

in which r is 1;

$G^a$ is ethylene or trans-vinylidene; and $Im^a$ is 4-imidazolyl;

or a pharmaceutically acceptable salt thereof.

A particularly preferred compound of the invention is one of those described herein as Example 1, 2, 7, 8, 10 or 15; and, more particularly, one described as Example 7 or 8; or a pharmaceutically acceptable salt thereof.

A compound of Formula I may be made by processes which include processes known in the chemical art for the production of structurally analogous compounds or by a novel process described herein. Novel processes and intermediates for the manufacture of a compound of Formula I as defined above provide further feature of the invention and are illustrated by the following procedures in which the meanings of the generic radicals are as defined above, unless otherwise specified. It will be recognized that it may be preferred or necessary to prepare a compound of Formula I in which a functional group is protected using a conventional protecting group, then to remove the protecting group to provide the compound of Formula I.

(A) For a compound of Formula I in which G is —(CH$_2$)$_s$— and s is 2, 3 or 4, hydrogenation of the double bond of a corresponding compound of Formula I in which G is —(CH$_2$)$_t$—CH=CH— and t is 0, 1 or 2. Conveniently, an acid addition salt of the compound of Formula I dissolved in aqueous ethanol is hydrogenated at ambient temperature and pressure over a palladium on carbon catalyst, for example as described in Example 2.

(B) Coupling an acid of Formula II,

X—C(O)—Y—C(O)—OH      II or an activated derivative thereof, with an amine of Formula III.

H$_2$N—CH$_2$—G—Im      III

The coupling is carried out using a conventional procedure, such as by using a mixed anhydride coupling, for example as described in Example 1, or by using a coupling reagent such as bis(2-oxo-3-oxazolidinyl)phosphinic chloride (BOP-Cl), for example as described in Example 10, or such as 1-(3-dimethylaminopropyl)-3-ethylcarbodiimide, for example as described in Example 16.

(C) Coupling an acid of Formula IV,

X—C(O)—OH      IV or an activated derivative thereof, with an amine of Formula V.

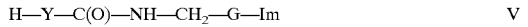

H—Y—C(O)—NH—CH$_2$—G—Im      V

The coupling is carried out using a conventional procedure, such as by using one of the methods described above in (B).

Whereafter, for any of the above procedures, when a functional group is protected using a protecting group, removing the protecting group.

Whereafter, for any of the above procedures, when a pharmaceutically acceptable salt of a compound of Formula I is required, it is obtained by reacting the acidic or basic form of such a compound of Formula I with a base or an acid affording a physiologically acceptable counterion or by any other conventional procedure, such as, for example, exchanging the counterion of a salt.

A compound corresponding to compound of Formula I in which one or more functional groups is protected provides another aspect of the invention. Such a compound may be represented as a compound of Formula Ip

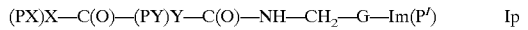

(P$^X$)X—C(O)—(P$^Y$)Y—C(O)—NH—CH$_2$—G—Im(P$^I$)      Ip which bears one or more of the protecting groups P$^X$, P$^Y$ and P$^I$ wherein P$^X$ is an optional protecting group(s) for a functional group(s) of X—C(O)—; P$^Y$ is an optional protecting group(s) for a functional group(s) of —Y—C(O)—; and P$^I$ is an optional protecting group(s) for a functional group of Im. Typical values for P$^X$ and P$^Y$ include the groups which form a t-butylester or benzyl ester when the protected functional group is carboxy, the groups which form a t-butyl urethane or a benzyl urethane when the protected functional group is amino, and the groups which form a methyl ether, t-butyl ether or benzyl ether when the protected functional group is hydroxy. Typical values for P$^I$ include the N-tosyl group to protect the imidazole N—H group. It will be recognized that a compound of Formula I may serve as a protected equivalent of another compound of Formula I. For example, a compound of Formula I in which A is R"OC(O)— wherein R" is t-butyl is a protected equivalent of a compound of Formula I in which A is hydrogen, as described in Example 1. Similarly, a compound of Formula I in which R$^m$ is —COOR$^b$ wherein R$^b$ t-butyl is a protected equivalent of a compound of Formula I in which R$^m$ is —COOR$^b$ and R$^b$ is hydrogen.

As mentioned above, the invention includes a pharmaceutically acceptable salt of a thrombin inhibiting compound defined by the above Formula I. A particular diamide of this invention possesses one or more sufficiently basic functional groups to react with any of a number of inorganic and organic acids which afford a nontoxic anion to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene sulfonic, methanesulfonic acid, oxalic acid, p-bromo phenyl sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of Formula I in which X or Y bears an acidic moiety, such a a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, the necessary starting materials for the preparation of a compound of Formula I may be prepared by procedures which are selected from standard techniques of organic chemistry, including aromatic and heteroaromatic substitution and transformation, from techniques which are analogous to the syntheses of known, structurally similar compounds, especially peptide syntheses, and techniques which are analogous to the above described procedures or procedures described in the Examples. It will be clear to one skilled in the art that a variety of sequences is available for the preparation of the starting materials. Starting materials which are novel provide another aspect of the invention.

A starting material acid of Formula II also may be represented as an acid of Formula IIa $$(P^X)X—C(O)—(P^Y)Y—C(O)—OH \qquad \text{IIp}$$

in which $P^X$ and $P^Y$ are optional protecting groups as defined above. Conveniently, an acid of Formula IIp may be prepared by coupling an optionally protected acid of Formula VI.

$$(P^X)X—C(O)—OH \qquad \text{VI}$$

with an amino acid derivative of Formula VII $$H—(P^Y)Y—C(O)—OP^C \qquad \text{VII}$$

in which $P^C$ is hydrogen or a carboxy protecting group, such as for example methyl, ethyl, t-butyl or benzyl, followed by removal of the protecting group $P^C$, when present.

An amine of Formula V may be prepared by coupling an N-protected amino acid of Formula VIII, $$(P^N)—Y—C(O)—OH \qquad \text{VIII}$$

wherein $P^N$ is an amino protecting group, with an amine of Formula III (which may bear a protecting group on Im), followed by removal of the protecting group $P^N$; for example, as described in Example 16.

An (optionally protected) amine of Formula III may be prepared by a number of routes which include those outlined in Scheme I in which Formula IIIp represents an optionally protected amine of Formula III.

Scheme I

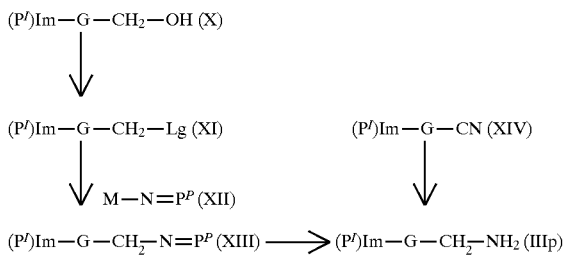

Thus, the hydroxy group of an alcohol of Formula X (in which the imidazole N—H group is conveniently protected by an N-tosyl group as $P^I$) is converted to a leaving group to provide a compound of Formula XI in which Lg is a leaving group, such as, for example bromo, iodo, mesylate or tosylate. The compound of Formula XI is then used to alkylate the nitrogen of a metallated, protected amine of Formula VII, in which M is a metal ion such as lithium, sodium or potassium and $N=P^P$ represents an amino bearing a protecting and activating group, such as a phthalimido group or a di-t-butyl iminodicarboxylate group, to afford the protected amine XIII. Removal of the protecting group $P^P$ then affords amine IIIp in which the N-tosyl group ($P^I$) may be retained or removed before coupling the amine. As an alternative route, a nitrile of Formula XIV may be reduced to afford an amine of Formula IIIp. Conveniently, both the double bond and the cyano group of a nitrile of Formula XIV in which G is —(CH$_2$)$_t$—CH=CH— and t is 0, 1 or 2 are reduced at the same time to afford a corresponding amine of Formula III in which s is 2, 3 or 4. Also, it will be seen that a compound of Formula XI can be converted into a homologous compound of Formula XIV by displacing the leaving group with cyanide ion, for example as described in Example 18.

A compound of the invention is isolated best in the form of an acid addition salt. A salt of the compound of Formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compound.

As noted above, the optically active isomers and diastereomers of the compounds of Formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of Formula I.

In another of its aspects, the invention provides a method of treating a thromboembolic disorder comprising administering to a mammal in need of treatment an effective (thromboembolic disorder therapeutic and/or prophylactic amount) dose of a compound of Formula I.

The invention in another of its aspects provides a method of inhibiting coagulation in mammals comprising administering to a mammal in need of treatment an effective (coagulation inhibiting) dose of a compound of Formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations.

Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical compositions for use in the above described therapeutic method. Pharmaceutical compositions of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 ml sterile glass ampoule. Another example of a unit dosage formulation comprises about 10 mg of a compound of the present invention as a pharmaceutically acceptable salt in 20 ml of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical composition comprising an effective amount of a compound of Formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The ability of a compound of the present invention to be an effective and orally active thrombin inhibitor is evaluated in one or more of the following assays.

The compounds provided by the invention (Formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 μl buffer (0.03M Tris, 0.15M NaCl, pH 7.4) with 25 μl of human thrombin solution (purified human thrombin, Enzyme Research Laboratories, South Bend, Indiana, at 8 NIH units/ml) and 25 μl of test compound in a solvent (50% aqueous methanol (v:v)). Then 150 μl of an aqueous solution of the chromogenic substrate (at 0.25 mg/ml) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

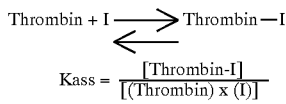

Kass is calculated for a range of concentrations of test compounds and the mean value reported in units of liter per mole. In general, a thrombin inhibiting compound of Formula I of the instant invention exhibits a Kass of $0.1 \times 10^6$ L/mole or much greater. For example, each of the particularly preferred examples of the invention listed above was determined to have a Kass of at least $5 \times 10^6$ L/mole. Thus, the compounds of Examples 7 and 8 were found to have a Kass of $57 \times 10^6$ L/mole and $80 \times 10^6$ L/mole, respectively.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Clu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Indiana; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Connecticut. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 ul thrombin (73 NIH unit/ml) to 100 ul human plasma which contains 0.0229 uCi 125-iodine labeled fibrinogen. Clot lysis is studied by overlaying the clots with 50 ul of urokinase or streptokinase (50, 100, or 1000 unit/ml) and incubating for 20 hours at room temperature. After incubation the tubes are centrifuged in a Beckman Microfuge. 25 ul of supernate is added into 1.0 ml volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/ml concentrations. Rough approximations of $IC_{50}$ values are estimated by linear extrapolations from data points to a value which would represent 50 percent of lysis for that particular concentration of fibrinolytic agent.

Anticoagulant Activity
Materials

Dog plasma and rat plasma are obtained from conscious mixed-breed hounds (either sex, hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Detroit, Mich.) is used for coagulation assays in plasma.

Methods
Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The thrombin time (TT) is measured by adding 0.05 ml saline and 0.05 ml thrombin (10 NIH units/ml) to 0.05 ml test plasma. The activated partial thromboplastin time (APTT) is measured by incubation of 0.05 ml test plasma with 0.05 ml Actin reagent for 120 seconds followed by 0.05 ml CaCl$_2$ (0.02M). The prothrombin time (PT) is measured by adding 0.05 ml saline and 0.05 ml Thromboplastin-C reagent to 0.05 ml test plasma. The compounds of formula I are added to human or animal plasma over a wide range of concentrations to determine prolongation effects on the TT, APTT and PT assays. Linear extrapolations are performed to estimate the concentrations required to double the clotting time for each assay. Each of the particularly preferred examples of the invention listed above was determined to have a TT value of less than 100 ng/mL. For example, the respective values (in ng/mL) for TT, APTT and PT were 30, 280 and 430 for the compound of Example 7 and 20, 170 and 380 for the compound of Example 8.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

FeCl$_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 ul is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269,1990).

Spontaneous thrombolysis model

In vitro data suggests that peptide thrombin inhibitors inhibit thrombin and at higher concentration may inhibit, other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 ml) is mixed rapidly with bovine thrombin (4 IU, Parke Davis) and $^{125}$I human Fibrogen (5 $\mu$Ci, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{\text{(injected cpm} - \text{lung cpm)}}{\text{injected cpm}} \times 100$$

The fibrinolytic dissolution of the implanted clot occurs time-dependently (see J. P. Clozel, *Cardiovas. Pharmacol.*, 12:520, 1988).

Coagulation parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 ml) is mixed with saline (0.1 ml) and bovine thrombin (0.1 ml, 30 U/ml in TRIS buffer; Parke Davis) at 37° C. For APTT, plasma (0.1 ml) and APTT solution (0.1 ml, Organon Teknika) are incubated for 5 minutes (37° C.) and CaCl$_2$ (0.1 ml, 0.025M) is added to start coagulation. Assays are done in duplicate and averaged.

Index of Bioavailability

A measure of bioactivity, plasma thrombin time (TT), serves as a substitute for the assay of parent compound on the assumption that increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\, po}{AUC\, iv} \times \frac{Dose\, iv}{Dose\, op} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 ml/kg for i.v., and 5 ml/kg for p.o. and infusion volume is 3 ml/hr.

Statistics

Results are expressed as means±SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50 percent relative humidity; and lighted from 0600–1800 hours.

Pharmacokinetic model

Test compound is formulated immediately prior to dosing by dissolving in sterile 0.9 percent saline to a 5 mg/ml preparation. Dogs are given a single 2 mg/kg dose of test compound by oral gavage. Blood samples (4.5 ml) are taken from the cephalic vein at 0.25, 0.5, 0.75, 1,2,3,4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood PO$_2$, PCO$_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for $\geq$30 minutes.

Hematology and template bleeding time determinations

Whole blood cell counts, hemoglobin, and hematocrit values are determined on a 40-$\mu$l sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of p<0.05. All values are mean±SEM. All studies are conducted in accordance with the guiding principles of the American Physiological Society. Further details regarding the procedures are described in Jackson, et al., *J. Cardiovasc. Pharmacol.*, 21, 587–599 (1993).

The following Examples are provided to further describe the invention and are not to be construed as limitations thereof.

The abbreviations used in the examples have the following meanings.

Amino acids: Azt=azetidine-2-carboxylic acid, Phe=phenylalamine, hPro=homo-proline, Pro=proline, Cha=β-cyclohexylalanine, Ohi=[2S-(2α,3aβ,7aβ)]-octahydroindol-2-carboxylic acid, 3-Piq=D-cis[4aR,8aR]-3-perhydroisoquinolinecarboxylate.

Anal.=elemental analysis
Boc=t-butyloxycarbonyl
Bn=benzyl
BOP-Cl=bis(2-oxo-3-oxazolidinyl)phosphinic chloride
t-Bu=t-butyl
n-BuLi=butyllithium
18–Crown-6=1,4,7,10,13,16-hexaoxacyclooctadecane
DIBAL=diisobutylaluminum hydride
DMF=dimethylformamide
DMSO=dimethylsulfoxide
Et=ethyl
EtOAc=ethyl acetate
Et$_2$O=diethyl ether
EtOH=ethanol
FAB-MS=fast atom bombardment mass spectrum
FD-MS=field desorption mass spectrum
HPLC=High Performance Liquid Chromatography
HRMS=high resolution mass spectrum
HOBT=1-hydroxybenzotriazole hydrate
i-PrOH=isopropanol
IR=Infrared Spectrum
Me=methyl
MeOH=methanol
NMR=Nuclear Magnetic Resonance
RPHPLC=Reversed Phase High Performance Liquid Chromatography
SiO$_2$=silica gel
TEA=triethylamine
TFA=trifluoroacetic acid
THF=tetrahydrofuran
TLC=thin layer chromatography
Ts=tosyl (p-toluenesulfonyl)

The following parameters for preparative RPHPLC were employed: Solvent A: 0.05% aqueous hydrochloric acid (1.5 mL concentrated hydrochloric acid in 3 L water); Solvent B: acetonitrile; Gradient: as defined in each Example; Column: Vydac C$_{18}$–5 cm×25 cm; Flow rate: 10 mL/minute.

Unless otherwise stated, pH adjustments and work up are with aqueous acid or base solutions. $^1$H-NMR indicates a satisfactory NMR spectrum was obtained for the compound described. IR indicates a satisfactory infra red spectrum was obtained for the compound described.

EXAMPLE 1

Preparation of D-Cha-Pro-4-(NHCH$_2$-trans-CHCH) imidazole.2HCl (D-cyclohexylalanyl-N-[(E)-3-(imidazol-4-yl)prop-2-enyl]-L-prolinamide dihydrochloride)

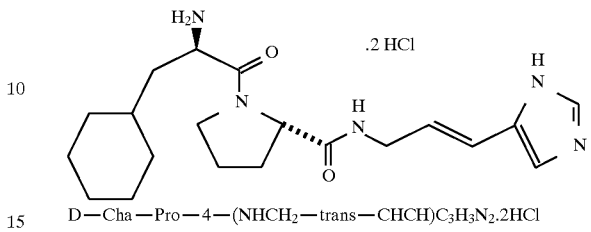

D—Cha—Pro—4—(NHCH$_2$—trans—CHCH)C$_3$H$_3$N$_2$.2HCl

A) Boc-D-Cha-Pro-OH

A solution of Boc-D-Cha-OH (50.4 g, 185 mmol) in dichloromethane (360 mL) was cooled to 0° C. and N-hydroxysuccinimide (22.3 g, 194 mmol) was added. Then 1,3-dicyclohexylcarbodiimide (39.0 g, 189 mmol) was added in two portions as a solution in dichloromethane (90 mL). After stirring for 3 h at 0° C., L-Pro-OH (27.6 g, 240 mmol) and N,N-diisopropylethylamine (30.9 g, 239 mmol) were added. After stirring an additional 3 h between 0° C. and 10° C., the mixture was filtered over diatomaceous earth. The filter cake was rinsed with dichloromethane (100 mL); then the combined filtrates were concentrated in vacuo. The residual oil was partitioned between ethyl acetate (100 mL) and 0.625M aqueous NaHCO$_3$ (320 mL). The layers were separated, and the organic phase was washed with 0.625M aq. NaHCO$_3$ (80 mL). The combined bicarbonate extracts were then washed with ethyl acetate (100 mL). The aqueous phase was then stirred with ethyl acetate (300 mL) and acidified with 12N HCl (approximately 37 mL). The layers were separated and the acidic aqueous phase was extracted with ethyl acetate (100 mL). The combined ethyl acetate extracts were concentrated in vacuo. The residue was slurried with a minimal amount of ethyl acetate, filtered, washed again with ethyl acetate and dried to give 50.1 g (73%) of white powder.

$^1$H-NMR
FAB-MS, m/e 369.2 (MH$^+$)
Analysis for C$_{19}$H$_{32}$N$_2$O$_5$: Calc: C, 61.93; H, 8.75; N, 7.60; Found: C, 62.01; H, 8.96; N, 7.75.

B) methyl urocanate.HCl

Anhydrous HCl was bubbled through a suspension of urocanic acid (69 g, 500 mmol) in methanol (1 L) until the solution was saturated. The stirring solution was then heated to reflux and the next morning, the solution was cooled and the solvents were removed in vacuo. The residue was washed twice with diethyl ether, filtered and dried in vacuo to give 93 g (98%) of white solid.

IR
$^1$H-NMR
FD-MS, m/e 152.0 (M$^+$)
Analysis for C$_7$H$_8$N$_2$O$_2$.HCl: Calc: C, 44.58; H, 4.81; N, 14.85; Found: C, 44.46; H, 4.82; N, 14.78.

C) methyl N-Ts-urocanate

To a stirring suspension of methyl urocanate.HCl (20 g, 106 mmol) in dichloromethane (300 mL) was added p-toluenesulfonyl chloride (21.2 g, 111 mmol) followed by triethylamine (24.4 mL, 180 mmol). After 16 h, the solvent was removed in vacuo and the residue was partitioned between ethyl acetate and water. The organic phase was washed twice with saturated NH$_4$Cl and twice with saturated NaHCO$_3$, then dried with Na$_2$SO$_4$, filtered and concentrated in vacuo. The residue was chromatographed over silica gel, eluting with 5% ethyl acetate/chloroform; and the product-containing fractions were combined and concentrated in vacuo to give 20.4 g (63%) of white solid.

IR
$^1$H-NMR
FD-MS, m/e 306 (M$^+$)
Analysis for $C_{14}H_{14}N_2O_4S$: Calc: C, 54.89; H, 4.61; N, 9.14; Found: C, 55.17; H, 4.64; N, 9.02.

D) 4-(HOCH$_2$-trans-CHCH)-1-Ts-imidazole

To a stirring solution of methyl N-Ts-urocanate (10 g, 33 mmol) in THF (250 mL) at 0° C. was added a solution of DIBAL (1M in toluene, 65 mL, 65 mmol). After 2 h, the solution was diluted with ethyl acetate (500 mL) and stirred vigorously with saturated aqueous sodium potassium tartrate (500 mL). After 30 min, the layers were separated and the organic phase was washed with brine, dried with Na$_2$SO$_4$, filtered and concentrated in vacuo to give 8.6 g (95%) of white solid.

IR
$^1$H-NMR
FD-MS, m/e 278 (M$^+$)
Analysis for $C_{13}H_{14}N_2O_3S$: Calc: C, 56.10; H, 5.07; N, 10.06; Found: C, 56.40; H, 5.21; N, 9.86.

E) 4-(BrCH$_2$-trans-CHCH)-1-Ts-imidazole

To a stirring solution of 4-(HOCH$_2$-trans-CHCH)-1-Ts-imidazole (7.0 g, 25 mmol) in THF (250 mL) was added carbon tetrabromide (12.5 g, 38 mmol) followed by triphenylphosphine (9.9 g, 38 mmol). After stirring for 2 h, the solvent was removed in vacuo and the residue was dissolved in chloroform, dry packed with silica gel, and chromatographed eluting with a step gradient of hexanes through 50% ethyl acetate/hexanes. The product-containing fractions were combined and concentrated in vacuo to give 7.8 g (61%) of white solid.

IR
$^1$H-NMR
FD-MS, m/e 342 (M$^+$)
Analysis for $C_{13}H_{13}BrN_2O_2S$: Calc: C, 45.76; H, 3.84; N, 8.21; Found: C, 46.03; H, 3.97; N, 8.25.

F) 4-(Boc$_2$NCH$_2$-trans-CHCH)-1-Ts-imidazole

To a stirring suspension of NaH (60% dispersion in oil, 0.7 g, 17.6 mmol) in THF (150 mL) was slowly added a solution of di-t-butyl iminodicarboxylate (3.82 g, 17.6 mmol) in THF (25 mL) followed by a solution of 4-(BrCH$_2$-trans-CHCH)-1-Ts-imidazole (4.0 g, 11.7 mmol) in THF (25 mL). After stirring for 20 h, the solvent was removed in vacuo and the residue was partitioned between ethyl acetate and water. The ethyl acetate phase was washed with saturated aqueous NH$_4$Cl, saturated aqueous NaHCO$_3$ and brine, then dried with MgSO$_4$, filtered and concentrated in vacuo. The residue was chromatographed over silica gel eluting with a step gradient of 10% ethyl acetate/hexanes through 50% ethyl acetate/hexanes and the product-containing fractions were combined and concentrated in vacuo to give 3.3 g (59%) of white solid.

IR
$^1$H-NMR
FD-MS, m/e 477 (M$^+$)
Analysis for $C_{23}H_{31}N_3O_6S$: Calc: C, 57.85; H, 6.54; N, 8.80; Found: C, 58.08; H, 6.55; N, 8.84.

G) 4-(H$_2$NCH$_2$-trans-CHCH)-1-Ts-imidazole.HCl

To a stirring solution of 4-(BoC$_2$NCH$_2$-trans-CHCH)-1-Ts-imidazole (4.74 g, 9.9 mmol) in dichloromethane (25 mL) at 0° C. was added trifluoroacetic acid (25 mL). After stirring for 1.5 h, the solvents were removed in vacuo and the residue was suspended in diethyl ether with vigorous stirring. The solid was filtered, washed again with diethyl ether, filtered and dried in vacuo to give 3.7 g (95%) of the TFA salt as a white solid.

A portion (500 mg) of the TFA salt was dissolved in water (50 mL) and 1N HCl (5 mL), washed with ethyl acetate, concentrated under vacuum to 20 mL, and lyopholized to give the indicated hydrochloride salt.

IR
$^1$H-NMR
FD-MS, m/e 278.1 (MH$^+$)

H) Boc-D-Cha-Pro-NH-4-(CH$_2$-trans-CHCH)-1-Ts-imidazole

In flask 1, 4-methylmorpholine (1.13 mL, mmol) was added to a stirring suspension of 4-(H$_2$NCH$_2$-trans-CHCH)-1-Ts-imidazole.HCl (1.3 g, 3.7 mmol) in DMF at 0° C. In Flask 2, to a stirring solution of Boc-D-Cha-Pro-OH (1.24 g, 3.4 mmol) and 4-methylmorpholine (0.38 mL, 3.4 mmol) in THF (25 mL) at −15° C. was added isobutyl chloroformate (0.44 mL, 3.4 mmol). After stirring for 5 min, the contents of flask 1 were added to flask 2 and the cold bath was removed. The next morning, the solvents were removed in vacuo and the residue was partitioned between ethyl acetate and saturated NH$_4$Cl. The organic phase was washed with brine, dried (Na$_2$SO$_4$), filtered and concentrated in vacuo to afford the coupled product.

I) D-Cha-Pro-NH-4-(CH$_2$-trans-CHCH)imidazole.2HCl

The residue from the above step was dissolved in THF (25 mL) and HOBT (0.92 g, 6.8 mmol) was added. After stirring for 6 h, the solvent was removed in vacuo and the residue was dissolved in dichloromethane (50 mL). To this stirring solution was added TFA (50 mL). After stirring for 12 h, the solvent was removed in vacuo and the residue was partitioned between 1N HCl and ethyl acetate. The aqueous phase was washed again with diethyl ether followed by ethyl acetate and concentrated in vacuo. The residue was then dissolved in water (30 mL) and purified by preparative RPHPLC (98/2 (A/B) through 60/40 (A/B), 150 min). The product-containing fractions were combined, partially concentrated and lyophilized to give 0.29 g (38%) of white solid.

$^1$H-NMR
FAB-MS, m/e 374.3 (MH$^+$)
Analysis for $C_{20}H_{31}N_5O_2$.2HCl: Calc: C, 53.81; H, 7.45; N, 15.69; Found: C, 53.58; H, 7.52; N, 15.45.

EXAMPLE 2

Preparation of D-Cha-Pro-NH-4-(CH$_2$CH$_2$CH$_2$)imidazole.2HCl (D-cyclohexylalanyl-N-[3-(imidazol-4-yl)propyl]-L-prolinamide dihydrochloride)

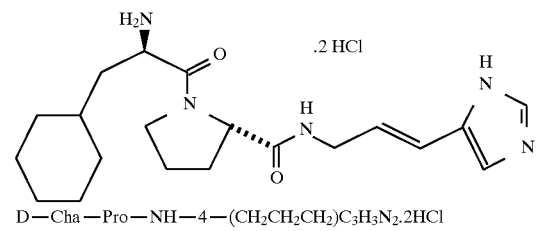

D—Cha—Pro—NH—4—(CH$_2$CH$_2$CH$_2$)C$_3$H$_3$N$_2$.2HCl

To a stirring solution of D-Cha-Pro-NH-4-(CH$_2$-trans-CHCH)imidazole.2HCl (150 mg, 0.34 mmol) in ethanol (70 mL) and water (30 mL) was added 5% Pd/C (0.5 g). The flask was evacuated and placed under an atmosphere of hydrogen. After 2 h, the solution was filtered through a pad of diatomaceous earth and the solvents were removed in vacuo. The residue was dissolved in water (10 mL), filtered through a 1μ filter and purified by preparative RPHPLC (98/2 (A/B) through 60/40 (A/B), 150 min). The product-containing fractions were combined, partially concentrated in vacuo and lyophilized to give 140 mg (92%) of white solid.

$^1$H NMR

FAB-MS, m/e 376.3 (MH$^+$)

Analysis for $C_{20}H_{33}N_5O_2 \cdot 2HCl$: Calc: C, 53.57; H, 7.87; N, 15.62; Found: C, 53.30; H, 7.89; N, 15.41.

EXAMPLE 3

Preparation of EtSO$_2$-D-Cha-Pro-4-(NHCH$_2$-trans-CHCH)imidazole.HCl

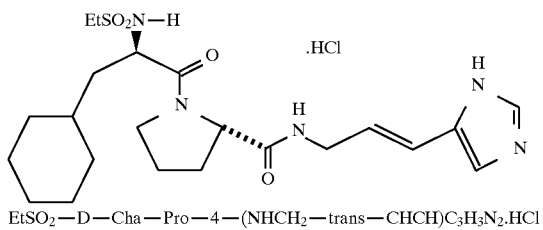

EtSO$_2$—D—Cha—Pro—4—(NHCH$_2$—trans—CHCH)C$_3$H$_3$N$_2$.HCl

A) EtSO$_2$-D-Phe-OH

To a stirring suspension of D-phenylalanine (50 g, 300 mmol) in THF (400 mL) was added N,O-bis(trimethylsilyl)acetamide (92 g, 450 mmol). After stirring for 12 h, the solution was cooled to −78° C. and N,N-diisopropylethylamine (58 mL, 330 mmol) was added. To this solution was slowly added ethanesulfonyl chloride (31 mL, 330 mmol) and the cold bath was removed. After stirring for 20 h, the solvents were removed in vacuo and the residue was partitioned between saturated aqueous NaHCO$_3$ and ethyl acetate. The aqueous phase was washed with diethyl ether, acidified with solid citric acid and extracted twice with ethyl acetate. The combined ethyl acetate extracts were washed with brine, dried with MgSO$_4$, filtered and concentrated in vacuo to give 61 g (79%) of a thick colorless oil.

IR $^1$H-NMR

FD-MS, m/e 257 (M$^+$)

B) EtSO$_2$-D-Phe-Pro-OBn

To a stirring suspension of EtSO$_2$-D-Phe-OH (25.7 g, 100 mmol), Pro-OBn.HCl (26.6 g, 110 mmol), HOBT (13.5 g, 100 mmol) and N,N-diisopropylethylamine (43.5 mL, 250 mL) in THF (1 L) at 0° C. was added 1-(3-dimethylaminopropyl)-3-ethylcarbodiimide hydrochloride (23 g, 120 mL). After stirring for 20 h, the solvent was removed in vacuo and the residue was partitioned between ethyl acetate and 1N citric acid. The organic phase was washed twice with 1N KHCO$_3$, twice with brine, dried with MgSO$_4$, filtered and concentrated in vacuo. The residue was chromatographed over silica gel, eluting with a step gradient of hexanes through 50% ethyl acetate/hexanes. The product-containing fractions were combined and concentrated in vacuo to give 29 g (65%) of a clear, thick oil.

IR $^1$H-NMR

FD-MS, m/e 444.2 (M$^+$)

C) EtSO$_2$-D-Phe-Pro-OH

To a solution of EtSO$_2$-D-Phe-Pro-OBn (28.5 g, 64 mmol) in ethyl acetate (500 mL) was added 10% Pd/C (5 g). The vessel was evacuated and placed under an atmosphere of hydrogen. After stirring for 16 h, the solution was filtered over diatomaceous earth, and the filter pad was then washed twice with methanol and filtered. The combined filtrates were concentrated in vacuo to give 22 g (97%) of off-white solid.

IR $^1$H-NMR

FD-MS, m/e 355.3 (MH$^+$)

Analysis for $C_{16}H_{22}N_2O_5S$: Calc: C, 54.22; H, 6.26; N, 7.90; Found: C, 53.98; H, 6.12; N, 7.63.

D) EtSO2-D-Cha-Pro-OH

To a solution of EtSO$_2$-D-Phe-Pro-OH (10 g, 28 mmol) in ethanol (300 mL) was added PtO$_2$ (5 g). The mixture was hydrogenated using a high pressure apparatus at 4.1 bar and 20° C. for 20 h. The solution was then filtered through diatomaceous earth and concentrated to give 8.1 g (80%) of thick oil.

IR $^1$H-NMR

FD-MS, m/e 361.2 (MH$^+$)

E) EtSO$_2$-D-Cha-Pro-4-(NHCH$_2$-trans-CHCH)imidazole.HCl

By methods substantially equivalent to those described in example 16-D, 420 mg (22%) of EtSO$_2$-D-Cha-Pro-4-(NHCH$_2$-trans-CHCH)imidazole.HCl was prepared from EtSO$_2$-D-Cha-Pro-OH and 4-(NH$_2$CH$_2$-trans-CHCH)-1-Ts-imidazole.HCl. The product was purified by preparative RPHPLC (90/10 (A/B) through 40/60 (A/B), 150 min).

$^1$H NMR

FD-MS, m/e 465.1 (M$^+$)

Analysis for $C_{22}H_{35}N_5O_4S \cdot 1.1HCl \cdot 1.0H_2O$: Calc: C, 50.45; H, 7.33; N, 13.37; Cl, 7.45; Found: C, 50.22; H, 6.97; N, 13.29; Cl, 7.36.

EXAMPLE 4

Preparation of EtSO$_2$-D-Cha-Pro-4-(NHCH$_2$CH$_2$CH$_2$)imidazole.HCl

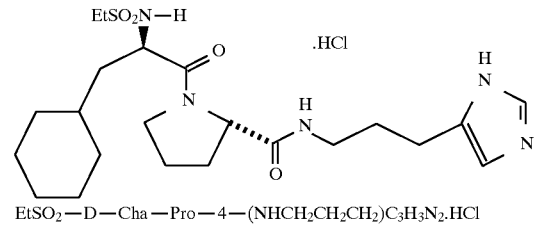

EtSO$_2$—D—Cha—Pro—4—(NHCH$_2$CH$_2$CH$_2$)C$_3$H$_3$N$_2$.HCl

By methods substantially equivalent to those described in example 2, 80 mg (80%) of EtSO$_2$-D-Cha-Pro-4-(NHCH$_2$CH$_2$CH$_2$)imidazole.HCl was prepared from EtSO$_2$-D-Cha-Pro-4-(NHCH$_2$-trans-CHCH)imidazole.HCl.

$^1$H NMR

FAB-MS, m/e 468.4 (MH$^+$)

Analysis for $C_{22}H_{37}N_5O_4S \cdot 1.1HCl \cdot 1.0H_2O$: Calc: C, 50.26; H, 7.69; N, 13.32; Found: C, 50.42; H, 7.31; N, 13.15.

EXAMPLE 5

Preparation of EtSO$_2$-D-Cha-Ohi-4-(NHCH$_2$-trans-CHCH)-imidazole.HCl

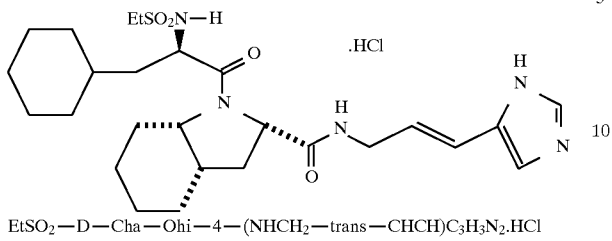

EtSO$_2$—D—Cha—Ohi—4—(NHCH$_2$—trans—CHCH)C$_3$H$_3$N$_2$.HCl

A) Preparation of [2S-(2α,3aβ,7aβ)]-octahydroindole-2-carboxylic acid ethyl ester.HCl (Ohi-OEt.HCl)

HCl gas was bubbled through a stirring suspension of (S)-indoline-2-carboxylic acid (20 g, 110 mmol) in ethanol (400 mL). When the acid was completely dissolved, the solution was brought to reflux. After 16 hours, the solution was cooled and the solvent removed in vacuo. The residue was triturated with diethyl ether and the resulting off-white solid was collected by filtration, washed with hexanes and dried overnight in a vacuum oven at 30° C. (25.5 g, 100%). This solid, (S)-indoline-2-carboxylic acid ethyl ester hydrochloride, was dissolved in ethanol (455 mL). To this was added 5% Pd/C (25.5 g) and the resulting suspension was hydrogenated at 4.1 bar on a shaker for 8 hours. The solution was filtered to remove catalyst and the filtrate was concentrated in vacuo. The residue was triturated with diethyl ether and the resulting solid was isolated by filtration to give 18.8 g (73%) of a white powder.

$^1$H NMR

FD-MS, m/e 197 (M$^+$)

Analysis for C$_{11}$H$_{19}$NO$_2$.HCl: Calc: C, 56.53; H, 8.63; N, 5.99; Found: C, 56.24; H, 8.44; N, 6.00.

B) EtSO$_2$-D-Phe-Ohi-OEt

By methods substantially equivalent to those described in example 3-B, 12.3 g (57%) of EtSO$_2$-D-Phe-Ohi-OEt was prepared from EtSO$_2$-D-Phe-OH and HCl.Ohi-OEt.

IR $^1$H NMR

FD-MS, m/e 436.1 (M$^+$)

Analysis for C$_{22}$H$_{32}$N$_2$O$_5$S: Calc: C, 60.53; H, 7.39; N, 6.42; Found: C, 60.62; H, 7.31; N, 6.22.

C) EtSO$_2$-D-Phe-Ohi-OH

To a stirring solution of EtSO$_2$-D-Phe-Ohi-OEt (12 g, 27.5 mmol) in p-dioxane (300 mL) was added a solution of LiOH.H$_2$O (2.3 g, 55 mmol) in water (150 mL). After stirring for 16 h, the solvent was removed in vacuo and the residue was redissolved in water and washed twice with diethyl ether. The aqueous phase was acidified with 5N HCl and the precipitate was filtered, washed with water and dried in vacuo to give 10.1 g (90%) of a light yellow solid.

IR $^1$H NMR

FD-MS, m/e 409.1 (M$^+$)

Analysis for C$_{20}$H$_{28}$N$_2$O$_5$S: Calc: C, 58.80; H, 6.91; N, 6.86; Found: C, 58.57; H, 7.00; N, 6.63.

D) EtSO$_2$-D-Cha-Ohi-OH

By methods substantially equivalent to those described in example 3-D, 8.9 g (95%) of EtSO$_2$-D-Cha-Ohi-OH was prepared from EtSO$_2$-D-Phe-Ohi-OH.

IR $^1$H-NMR

FD-MS, m/e 415.3 (MH$^+$)

E) EtSO$_2$-D-Cha-Ohi-4-(NHCH$_2$-trans-CHCH)imidazole.HCl

By methods substantially equivalent to those described in example 3-E, 160 mg (49%) of EtSO$_2$-D-Cha-Ohi-4-(NHCH$_2$-trans-CHCH)imidazole.HCl was prepared from EtSO$_2$-D-Cha-Ohi-OH and 4-(NHCH$_2$-trans-CHCH)-1-Ts-imidazole.HCl. The product was purified by preparative RPHPLC (90/10 (A/B) through 40/60 (A/B), 150 min).

$^1$H NMR

FAB-MS, m/e 520.4 (MH$^+$)

Analysis for C$_{26}$H$_{41}$N$_5$O$_4$S.HCl: Calc: C, 56.15; H, 7.61; N, 12.59; Found: C, 56.06; H, 7.69; N, 12.44.

EXAMPLE 6

Preparation of EtSO$_2$-D-Cha-Ohi-4-(NHCH$_2$CH$_2$CH$_2$)imidazole.HCl

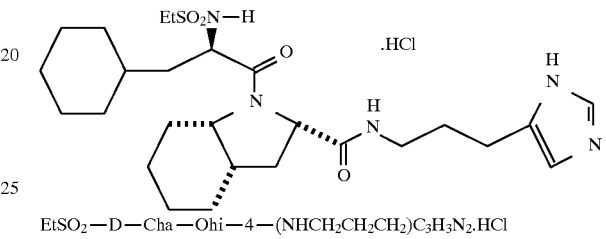

EtSO$_2$—D—Cha—Ohi—4—(NHCH$_2$CH$_2$CH$_2$)C$_3$H$_3$N$_2$.HCl

By methods substantially equivalent to those described in example 2, 75 mg (92%) of EtSO$_2$-D-Cha-Ohi-4-(NHCH$_2$CH$_2$CH$_2$)-imidazole.HCl was prepared from EtSO$_2$-D-Cha-Ohi-4-(NHCH$_2$-trans-CHCH)imidazole.HCl.

$^1$H NMR

FAB-MS, m/e 522.4 (MH$^+$)

Analysis for C$_{26}$H$_{43}$N$_5$O$_4$S.2.5HCl.1.0H$_2$O: Calc: C, 49.50; H, 7.59; N, 11.10; Found: C, 49.89; H, 7.23; N, 11.07.

EXAMPLE 7

Preparation of HO$_2$CCH$_2$-D-Cha-Pro-4-(NHCH$_2$-trans-CHCH)-imidazole.HCl (N-(carboxymethyl)-D-cyclohexylalanyl-N-[(E)-3-(imidazol-4-yl)prop-2-enyl]-L-prolinamide hydrochloride)

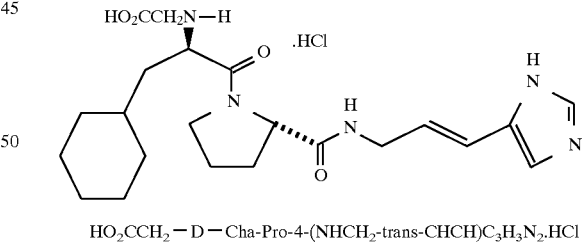

HO$_2$CCH$_2$ — D — Cha-Pro-4-(NHCH$_2$-trans-CHCH)C$_3$H$_3$N$_2$.HCl

A) Boc-D-Phe-Pro-OBn

To a solution of Boc-D-Phe-OH (89.1 g, 336 mmol), Pro-OBn.HCl (81.2g, 336 mmol), HOBT (50 g, 370 mmol) and N,N-diisopropylethylamine (176 mL, 1,008 mmol) at 0° C. in dichloromethane (600 mL) was added 1-(3-dimethylaminopropyl)-3-ethylcarbodiimide.HCl (71 g, 370 mmol). After stirring for 18 h, the mixture was diluted with diethyl ether (1 L) and washed three times with 1N citric acid (250 mL), once with water (250 mL), three times with saturated aqueous NaHCO$_3$ (250 mL) and once with saturated aqueous NaCl (250 mL). The organic phase was dried (Na2SO$_4$), filtered, and concentrated in vacuo to yield 140 g (92.5%) of a pale yelow foam.

FD-MS, m/e 452 (M+)

¹H NMR

B) D-Phe-Pro-OBn.HCl

Through a stirring solution of Boc-D-Phe-Pro-OBn (74 g, 5 mmol) in p-dioxane (400 mL) was bubbled HCl gas, while the solution was cooled with a 0° C. bath. After 15 min, HCl bubbling was stopped and the cold bath was removed. After an additional 3 h, the solvent was removed in vacuo. The residue was washed several times with diethyl ether and dried in vacuo to give 61 g (98%) of a yellow foam.

¹H-NMR

FD-MS, m/e 353 (MH+)

Analysis for $C_{21}H_{24}N_2O_3 \cdot HCl$: Calc: C, 64.86; H, 6.48; N, 7.20; Found: C, 65.48; H, 6.75; N, 7.94.

C) N-(t-BuO₂CCH₂)-N-Boc-D-Phe-Pro-OBn

To a solution of D-Phe-Pro-OBn.HCl (20 g, 51 mmol) in DMF (100 mL) was added t-butyl bromoacetate (9.9 g, 56 mmol) in one portion and N,N-diisopropylethylamine (17.4 mL, 101 mmol) dropwise over 30 min. This mixture was allowed to stir for 18 h at room temperature. Di-t-butyl dicarbonate (16.6 g, 76 mmol) and N,N-diisopropylethylamine (13.2 mL, 76 mmol) were then added in one portion and the reaction was allowed to stir an additional 24 h. The solvent was removed in vacuo and the residue was partitioned between ethyl acetate (1 L) and 1M aqueous citric acid (500 mL). The layers were separated and the organic phase was washed once with 1M aqueous citric acid, twice with saturated aqueous sodium bicarbonate, and once with brine (500 mL each). The organic phase was dried (Na2SO4), filtered, and concentrated in vacuo. The amber oil was purified by silica gel chromatography eluting with a ethyl acetate/hexanes gradient (hexanes to 30% ethyl acetate/hexanes). Fractions containing product were combined and concentrated to give 19.0 g (66%) as a colorless oil which slowly crystallized upon standing.

¹H NMR

FD-MS, m/e 566 (M+)

Analysis for $C_{32}H42N2O7$: Calc: C, 67.82; H, 7.47; N, 4.94; Found: C, 68.06; H, 7.33; N, 5.17.

D) N-(t-BuO₂CCH₂)-N-Boc-D-Cha-Pro-OH

By methods substantially equivalent to those described in example 3-C and 3-D, 22 g (63%) of N-(t-BuO₂CCH₂)-N-Boc-D-Cha-Pro-OH was prepared from N-(t-BuO₂CCH₂)-N-Boc-D-Phe-Pro-OBn.

¹H-NMR

FD-MS, m/e 483 (M+)

Analysis for $C_{25}H_{42}N_2O_7$: Calc: C, 62.22; H, 8.77; N, 5.80; Found: C, 62.99; H, 8.96; N, 5.48.

E) HO₂CCH₂-D-Cha-Pro-4-(NHCH₂-trans-CHCH)imidazole.HCl

By methods substantially equivalent to those described in example 1-H and 1-I, 0.31 g (36%) of HO₂CCH₂-D-Cha-Pro-4-(NHCH₂-trans-CHCH)imidazole.HCl was prepared from N-(t-BuO₂CCH₂)-N-Boc-D-Cha-Pro-OH and 4-(NHCH₂-trans-CHCH)-1-Ts-imidazole.HCl. The product was purified by preparative RPHPLC (98/2 (A/B) through 60/40 (A/B), 150 min).

¹H NMR

FAB-MS, m/e 432.3 (MH+)

Analysis for $C_{22}H_{33}N_5O_4 \cdot 1.5HCl$: Calc: C, 54.35; H, 7.15; N, 14.40; Found: C, 53.98; H, 7.21; N, 14.03.

EXAMPLE 8

Preparation of HO₂CCH₂-D-Cha-Pro-4-(NHCH₂CH₂CH₂)imidazole.HCl (N-(carboxymethyl)-D-cyclohexylalanyl-N-[3-(imidazol-4-yl)propyl]-L-prolinamide hydrochloride)

HO₂CCH₂—D—Cha-Pro-4-(NHCH₂CH₂CH₂)C₃H₃N₂.HCl

By methods substantially equivalent to those described in example 2, 0.29 g (99%) of HO₂CCH₂-D-Cha-Pro-4-(NHCH₂CH₂CH₂)C₃H₃N₂-HCl was prepared from HO₂CCH₂-D-Cha-Pro-4-(NHCH₂-trans-CHCH)imidazole.HCl.

¹H NMR

FAB-MS, m/e 434.4 (MH+)

Analysis for $C_{22}H_{35}N_5O_4 \cdot 2.5HCl \cdot 1.0H_2O$: Calc: C, 48.69; H, 7.34; N, 12.90; Found: C, 48.83; H, 6.99; N, 12.86.

EXAMPLE 9

Preparation of D-Cha-Ohi-4-(NHCH₂-trans-CHCH)imidazole.2HCl

D—Cha-Ohi-4-(NHCH₂-trans-CHCH)C₃H₃N₂.2HCl

A) 4-(NH₂CH₂-trans-CHCH)imidazole.2HCl

To a stirring solution of 4-(Boc₂NCH₂-trans-CHCH)-1-Ts-imidazole (4.9 g, 10 mmol) in THF (200 mL) was added HOBT (2,8 g, 20 mmol). After 16 h, the solvent was partially concentrated in vacuo and 1N HCl was added. After stirring for another 24 h, the solvent was removed in vacuo and the residue redissolved in 1N HCl. The aqueous phase was washed several times with n-butanol and once with ethyl acetate. The aqueous phase was then concentrated to give 2 g (100%) of a tan solid.

IR

¹H-NMR

FD-MS, m/e 123.0 (M+)

B) D-Cha-Ohi-4-(NHCH₂-trans-CHCH)imidazole.2HCl

By methods substantially equivalent to those described in examples 5-B, 5-C, 1-H and 1-I (but without treatment with HOBT), 112 mg of D-Cha-Ohi-4-(NHCH₂-trans-CHCH)imidazole.2HCl was prepared from Boc-D-Cha-OH and HCl.Ohi-OEt, and 4-(NH₂CH₂-trans-CHCH)imidazole.2HCl. The product was purified by preparative RPHPLC (98/2 (A/B) through 60/40 (A/B), 150 min).

¹H-NMR

FD-MS, m/e 428 (M+)

Analysis for $C_{24}H_{37}N_5O_2 \cdot 3HCl \cdot 0.5H_2O$: Calc: C, 52.80; H, 7.57; N, 12.82; Found: C, 53.30; H, 6.90; N, 12.52.

EXAMPLE 10

Preparation of D-Cha-Ohi-4-(NHCH₂CH₂CH₂) imidazole.2HCl (1-(D-cyclohexylalanyl)-N-[3-(imidazol-4-yl)-propyl]-[2S-(2α,3aβ,7aβ)]-octahydroindol-2-carboxamide dihydrochloride)

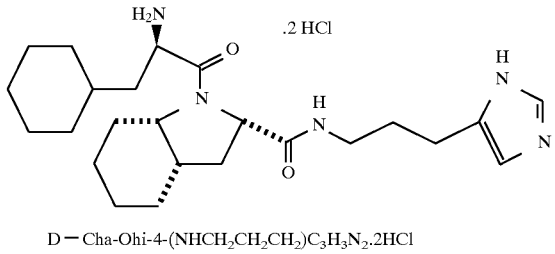

D—Cha-Ohi-4-(NHCH₂CH₂CH₂)C₃H₃N₂.2HCl

A) 4-HOCH₂-1-Ts-imidazole

To a solution of 4-HOCH₂-imidazole.HCl (18 g, 134 mmol) and K₂CO₃ (55.4 g, 400 mmol) in water (100 mL) was added a solution of p-toluenesulfonyl chloride (25.4 g, 134 mmol) in THF (300 mL) with vigorous stirring. After stirring overnight, the solution was partially concentrated in vacuo and extracted three times with ethyl acetate. The combined ethyl acetate phase was then washed twice with brine, dried with MgSO₄, filtered and concentrated in vacuo to give 32 g (95%) of a white solid.
¹H-NMR B) 4-OHC-1-Ts-imidazole To a stirring solution of oxalyl chloride (8.3 mL, 95 mmol) in dichloromethane (250 mL) at −78° C., was added dropwise DMSO (22 mL, 280 mmol). After 5 min, a solution of 4-HOCH₂-1-Ts-imidazole (20 g, 79 mmol) in dichloromethane (50 mL) was added over 2 min via an addition funnel. After 20 min, triethylamine (66 mL, 470 mmol) was added and the cold bath was removed. After the solution warmed to room temperature, water (300 mL) was added and the layers were separated. The aqueous phase was extracted three times with dichloromethane and the combined organic phase was washed twice with brine, then dried over MgSO₄, filtered and evaporated in vacuo to give 19.8 g (100%) of a tan solid.

C) 4-NCCHCH-1-Ts-imidazole

To a stirring suspension of NaH (3.5 g, 87 mmol, 60% dispersion in oil) in THF (200 mL) was added via addition funnel a solution of 4-OHC-1-Ts-imidazole (19.8 g, 79 mmol) and diethyl cyanomethylphosphonate (14 g, 79 mmol) in THF (100 mL). After 2 h, the reaction was quenched by the addition of 1N citric acid. The solvent was evaporated in vacuo and the residue was partitioned between ethyl acetate and 1N citric acid. The organic phase was washed twice with 1N citric acid, once with water, twice with sat. NaHCO₃ and once with brine. The organic phase was then dried with MgSO₄, filtered and concentrated to a small volume in vacuo. Diethyl ether was added and the resulting precipitate was filtered and dried in vacuo to give 13.1 g (61%) of a white solid.
1H-NMR
IR
FD-MS 273 (M⁺)

D) 4-NH₂CH₂CH₂CH₂-imidazole.2HCl

To a solution of 4-NCCHCH-1-Ts-imidazole (2.5 g, 9.1 mmol) in THF (50 mL) was added HOBT (3.6 g, 27 mmol). After stirring overnight, another portion of HOBT (1.2 g, 9.1 mmol) was added and the solution continued to stir for 2 h. The solvent was evaporated in vacuo and the residue was partitioned between 1N HCl and ethyl acetate. The layers were then separated and the aqueous phase was washed with butanol, washed twice with ethyl acetate and then concentrated in vacuo. The residue was dissolved in ethanol (50 mL) and PtO₂ (0.11 g) was added. The solution was then placed under an atmosphere of hydrogen (5.2 bar) for 4 h and then filtered through diatomaceous earth followed by an acrodisk and concentrated in vacuo to give 1.1 g (75%) of a white solid.
¹H-NMR E) Boc-D-Cha-Ohi-OH By methods substantially equivalent to those described in examples 3-B and 5-C substituting Boc-D-Cha-OH for EtSO₂-D-Phe-OH, 6.4 g of Boc-D-Cha-Ohi-OH were prepared.
¹H-NMR
IR
FD-MS, m/e 423 (M⁺)
Analysis for C₂₃H₃₈N₂O₅: Calc: C, 65.38; H, 9.06; N, 6.63; Found: C, 65.62; H, 9.01; N, 6.55.

F) D-Cha-Ohi-4-(NHCH₂CH₂CH₂)imidazole.2HCl

To a stirring solution of Boc-D-Cha-Ohi-OH (1.27 g, 3 mmol), 4-NH₂CH₂CH₂CH₂-imidazole.2HCl (0.53 g, 3 mmol), and N,N-diisopropylethylamine (2 mL, 3.3 mmol) in DMF (15 mL) was added BOP-Cl (1.71 g, 3.3 mmol). After stirring overnight, the solvent was removed in vacuo and the residue was partitioned between ethyl acetate and saturated NH₄Cl. The organic phase was washed again with saturated NH₄Cl, once with water, twice with saturated NaHCO₃ and once with brine. The solution was dried with MgSO₄, filtered and concentrated in vacuo. The residue was dissolved in TFA (25 mL) and after stirring for 2 h, the solvent was removed in vacuo. The residue was then dissolved in 1N HCl, extracted several times with ethyl acetate, partially concentrated and purified by preparative RPHPLC (98/2 (A/B) through 60/40 (A/B), 150 min). Lyophilization of the product-containing fractions provided 430 mg (29%) of D-Cha-Ohi-4-(NHCH₂CH₂CH₂)-imidazole.2HCl.
IR
FD-MS, m/e 430 (MH⁺)
Analysis for C₂₄H₃₉N₅O₂.2.8HCl: Calc: C, 54.22; H, 7.92; N, 13.17; Found: C, 54.63; H, 7.40; N, 12.83.

EXAMPLE 11

Preparation of D-Cha-Azt-4-(NHCH₂-trans-CHCH) imidazole.2HCl

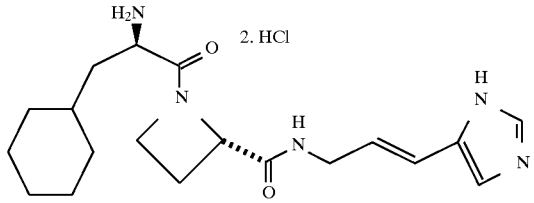

D—Cha-Azt-4-(NHCH₂-trans-CHCH)C₃H₃N₂.2HCl

A) Boc-D-Cha-Azt-OH

By methods substantially equivalent to those described in example 1-B, 3-B, and 5-C, 4 g of Boc-D-Cha-Azt-OH was prepared from Azt-OH and Boc-D-Cha-OH.
IR
¹H-NMR
FD-MS, m/e 355.2 (MH⁺)

B) D-Cha-Azt-4-(NHCH₂-trans-CHCH)imidazole.2HCl

By methods substantially equivalent to those described in example 9-B, 95 mg of D-Cha-Azt-4-(NHCH₂-trans-CHCH)imidazole.2HCl was prepared from Boc-D-Cha-Azt-OH and 4-(NH₂CH₂-trans-CHCH)imidazole.2HCl. The product was purified by preparative RPHPLC (98/2 (A/B) through 60/40 (A/B), 150 min).

¹H-NMR

FD-MS, m/e 360.2 (MH⁺)

Analysis for $C_{19}H_{29}N_5O_2 \cdot 3.0HCl \cdot 0.5H_2O$: Calc: C, 47.76; H, 6.96; N, 14.65; Found: C, 47.36; H, 6.69; N, 14.42.

EXAMPLE 12

Preparation of D-Cha-Azt-4-NHCH₂CH₂CH₂-imidazole.2HCl

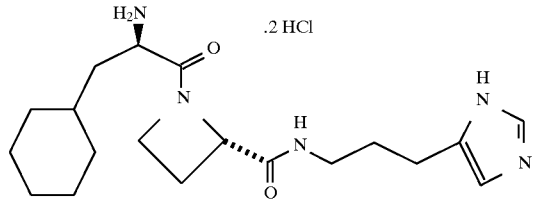

D—Cha-Azt-4-NHCH₂CH₂CH₂)C₃H₃N₂.2HCl

D-Cha-Azt-4-NHCH₂CH₂CH₂-imidazole.2HCl

By methods substantially equivalent to those described in example 10-E, substituting Boc-D-Cha-Azt-OH for Boc-D-Cha-Ohi-OH, 30 mg of D-Cha-Azt-4-NHCH₂CH₂CH₂-imidazole.2HCl was prepared. The product was purified by preparative RPHPLC (98/2 (A/B) through 60/40 (A/B), 150 min).

¹H-NMR

ES-MS, m/e 362.2 (MH⁺)

Analysis for $C_{19}H_{31}N_5O_2 \cdot 3.5HCl \cdot 3.0H_2O$: Calc: C, 42.02; H, 7.52; N, 12.89; Found: C, 42.24; H, 7.04; N, 12.74.

EXAMPLE 13

Preparation of D-Cha-hPro-4-(NHCH₂-trans-CHCH)imidazole.2HCl

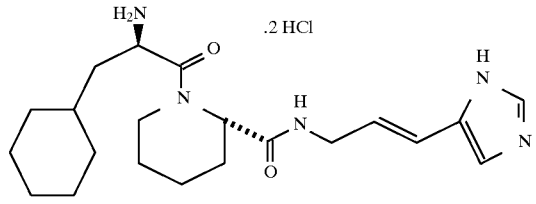

D—Cha-hPro-4-(NHCH₂-trans-CHCH)C₃H₃N₂.2HCl

By methods substantially equivalent to those described in example 9, 0.18 g of D-Cha-hPro-4-(NHCH₂-trans-CHCH) imidazole.2HCl were prepared fwas pPro-OH. The product was purified by preparative RPHPLC (98/2 (A/B) through 60/40 (A/B), 150 min).

¹H-NMR

FD-MS, m/e 388.2 (MH⁺)

Analysis for $C_{21}H_{33}N_5O_2 \cdot 2.0HCl \cdot 2.5H_2O$: Calc: C, 49.90; H, 7.98; N, 13.85; Found: C, 49.67; H, 7.62; N, 13.77.

EXAMPLE 14

Preparation of D-Cha-hPro-4-NHCH₂CH₂CH₂-imidazole.2HCl

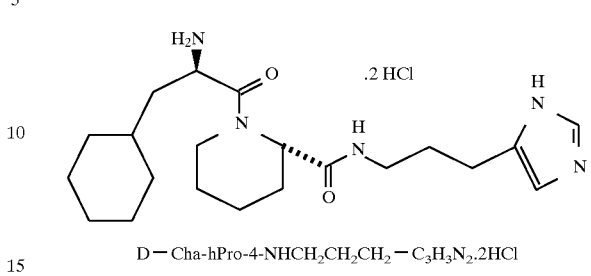

D—Cha-hPro-4-NHCH₂CH₂CH₂—C₃H₃N₂.2HCl

By methods substantially equivalent to those described in example 10, 118 mg of D-Cha-hPro-4-NHCH₂CH₂CH₂-C₃H₃N₂.2HCl were prepared from hPro-OH. The product was purified by preparative RPHPLC (98/2 (A/B) through 60/40 (A/B), 150 min).

¹H-NMR

FD-MS, m/e 390.5 (MH⁺)

Analysis for $C_{21}H_{35}N_5O_2 \cdot 2.5HCl$: Calc: C, 52.47; H, 7.86; N, 14.57; Found: C, 51.92; H, 7.71; N, 14.34. Found: C, 53.42; H, 7.68; N, 14.79.

EXAMPLE 15

Preparation of HO₂CCH₂-D-Cha-Pro-4-NHCH₂CH₂-imidazole.2HCl (N-(carboxymethyl)-D-cyclohexylalanyl-N-[2-(imidazol-4-yl)ethyl]-L-prolinamide dihydrochloride)

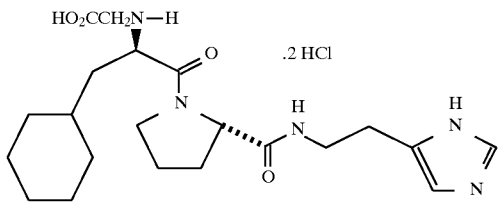

HO₂CCH₂—D—Cha—Pro-4-NHCH₂CH₂-imidazole.2HCl

By methods substantially equivalent to those described in example 1-H and 1-I (using N-(t-BuO₂CCH₂)-N-Boc-D-Cha-Pro-OH in place of Boc-D-Cha-Pro-OH and DMF in place of THF and omitting treatment with HOBT), 0.8 g of HO₂CCH₂-D-Cha-Pro-4-NHCH₂CH₂-imidazole.HCl was prepared from histamine hydrochloride. The final product was purified by RPHPLC (98/2 (A/B) through 70/30 (A/B), 2 h).

IR

¹H NMR

FAB-MS, m/e 420.2 (MH⁺)

Analysis for $C_{21}H_{33}N_5O_4 \cdot 2.1HCl \cdot 0.8H_2O$: Calc: C, 49.41; H, 7.25; N, 13.72; Cl, 14.58; Found: C, 49.49; H, 6.89; N, 13.64; Cl, 14.72.

EXAMPLE 16

Preparation of EtSO$_2$-D-Cha-Pro-4-(NHCH$_2$CH$_2$)imidazole.HCl

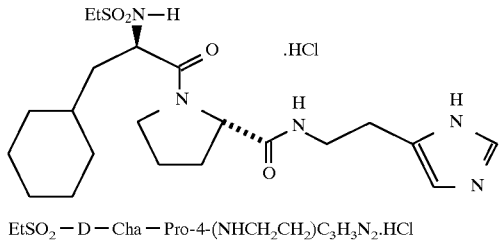

EtSO$_2$—D—Cha—Pro-4-(NHCH$_2$CH$_2$)C$_3$H$_3$N$_2$.HCl

A) Boc-Pro-4-(NHCH$_2$CH$_2$)imidazole

By methods substantially equivalent to those described in example 3-B, using DMF in place of THF, Boc-Pro-4-(NHCH$_2$CH$_2$)imidazole was prepared from Boc-Pro-OH and histamine.2HCl.

$^1$H-NMR

FD-MS, m/e 309 (MH$^+$)

B) Boc-Pro-4-(NHCH$_2$CH$_2$)-1-Ts-imidazole

To a stirring solution of Boc-Pro-4-(NHCH$_2$CH$_2$)imidazole (7.7 g, 25 mmol) in dichloromethane (100 mL) was added p-toluenesulfonyl chloride (4.3 g, 25 mmol) followed by triethylamine (6.3 mL, 50 mmol). After stirring for 16 h, the solvent was removed in vacuo and the residue was partitioned between ethyl acetate and saturated aqueous NH$_4$Cl. The organic phase was washed again with saturated aqueous NH$_4$Cl, twice with saturated aqueous NaHCO$_3$, dried with Na$_2$SO$_4$, filtered and concentrated in vacuo. The residue was chromatographed over silica gel, eluting with a step gradient of chloroform through 20% methanol/chloroform. The product containing fractions were combined and concentrated in vacuo to give 7.65 g (66%) of an off-white solid.

$^1$H-NMR

FD-MS, m/e 460 (M$^+$)

C) Pro-4-(NHCH$_2$CH$_2$)-1-Ts-imidazole.TFA

To a stirring solution of Boc-Pro-4-(NHCH$_2$CH$_2$)-1-Ts-imidazole (4.0 g, 8.6 mmol) in dichloromethane (20 mL) at 0° C. was added TFA (20 mL). After stirring for 1 h, the solvents were removed in vacuo and the thick oily residue was washed several times with diethyl ether and dried in vacuo to give a thick oil.

$^1$H-NMR

D) EtSO$_2$-D-Cha-Pro-4-(NHCH$_2$CH$_2$)imidazole.HCl

Pro-4-(NHCH$_2$CH$_2$)-1-Ts-imidazole.TFA (1.43 g, 3.0 mmol) was partitioned between dichloromethane (100 mL) and saturated aqueous NaHCO$_3$ (100 mL). The organic phase was separated, dried with MgSO$_4$, filtered. To this solution was added EtSO$_2$-D-Cha-OH (prepared from EtSO$_2$-D-Phe-OH by methods substantially equivalent to those in example 3-D) (0.79 g, 3.0 mmol), followed by 1-(3-dimethylaminopropyl)-3-ethylcarbodiimide hydrochloride (0.58 g, 3.0 mmol). After stirring for 16 h, the solvents were removed and the residue was partitioned between ethyl acetate and saturated aqueous NH$_4$Cl. The organic phase was washed with brine, dried with MgSO$_4$, filtered and concentrated in vacuo. The residue was dissolved in THF and to this solution was added HOBT. After stirring for 16 h, the solvent was removed in vacuo and the residue was partitioned between ethyl acetate and water. The aqueous phase was then acidified to pH 2 with 1N HCl and washed 4 times with ethyl acetate. The aqueous phase was then partially concentrated, filtered through an acrodisc and purified by preparative RPHPLC (90/10 (A/B) through 40/60 (A/B), 150 min). The product containing fractions were combined, partially concentrated and lyophilized to give 180 mg (12%) of EtSO2-D-Cha-Pro-4-(NHCH$_2$CH$_2$)C$_3$H$_3$N$_2$.HCl.

$^1$H-NMR

FD-MS, m/e 454.1 (MH$^+$)

Analysis for C$_{21}$H$_{35}$N$_5$O$_4$S.1.3HCl 1.0H$_2$O: Calc: C, 48.60; H, 7.44; N, 13.49; Cl, 8.88; Found: C, 48.50; H, 7.40; N, 13.50; Cl, 9.20.

EXAMPLE 17

Preparation of D-Cha-Pro-4-NHCH$_2$CH$_2$CH$_2$-5-CH$_3$-imidazole.2HCl

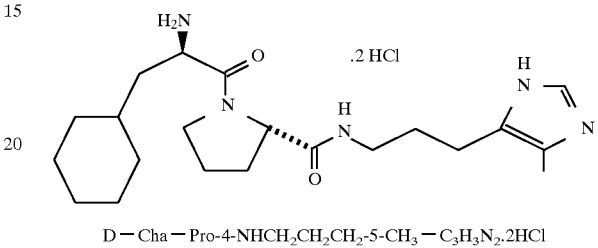

D—Cha—Pro-4-NHCH$_2$CH$_2$CH$_2$-5-CH$_3$—C$_3$H$_3$N$_2$.2HCl

By methods substantially equivalent to those described in example 10 substituting 5-Me-4-HOCH$_2$-imidazole.HCl for 4-HOCH$_2$-imidazole.HCl and substituting Boc-D-Cha-Pro-OH for Boc-D-Cha-Ohi-OH, 118 mg of D-Cha-Pro-4-NHCH$_2$CH$_2$CH$_2$5-Me-C$_3$H$_3$N$_2$.2HCl were prepared. The product was purified by preparative RPHPLC (98/2 (A/B) through 60/40 (A/B), 150 min).

$^1$H-NMR

FD-MS, m/e 390 (M$^+$)

Analysis for C$_{21}$H$_{35}$N$_5$O$_2$.30HCl.1.7H$_2$O: Calc: C, 47.63; H, 7.88; N, 13.22; Found: C, 47.98; H, 7.62; N, 12.94.

EXAMPLE 18

Preparation of D-Cha-Pro-4-NHCH$_2$CH$_2$CH$_2$CH$_2$-imidazole.2HCl

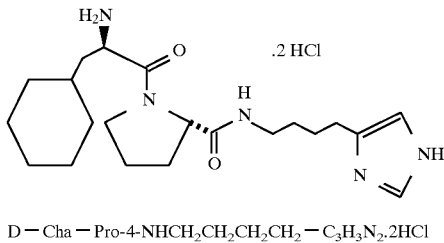

D—Cha—Pro-4-NHCH$_2$CH$_2$CH$_2$CH$_2$—C$_3$H$_3$N$_2$.2HCl

A) 4-NCCH$_2$CHCH-1-Ts-imidazole

To a stirring solution of 4-(BrCH$_2$-trans-CHCH)-1-Ts-imidazole (4.5 g, 13.2 mmol) in DMF (50 mL) was added KCN (1.0 g, 15.8 mmol) followed by 18-Crown-6 (0.7 g, 2.64 mmol). After stirring overnight, the solvent was removed in vacuo and the residue was dissolved in ethyl acetate and washed with brine. The organic phase was then dried (MgSO$_4$), filtered and concentrated in vacuo. The residue was purified by silica gel chromatography eluting with an ethyl acetate/hexanes gradient. The product-containing fractions were combined and concentrated in vacuo to give 1.8 g (47%) of white solid.

$^1$H-NMR

B) D-Cha-Pro-4-NHCH$_2$CH$_2$CH$_2$CH$_2$-imidazole.2HCl

By methods substantially equivalent to those described in example 10-D, 10-E and 10-F, substituting 4-NCCH$_2$CHCH-1-Ts-imidazole for 4-NCCHCH-1-Ts-imidazole, 130 mg of D-Cha-Pro-4-NHCH$_2$CH$_2$CH$_2$CH$_2$-C$_3$H$_3$N$_2$.2HCl were prepared. The product was purified by preparative RPHPLC (98/2 (A/B) through 60/40 (A/B), 150 min).

$^1$H-NMR

FD-MS, m/e 390 (M$^+$)

Analysis for C$_{21}$H$_{35}$N$_5$O$_2$.2.0HCl.0.8H$_2$O: Calc: C, 52.89; H, 8.16; N, 14.68; Found: C, 52.73; H, 7.86; N, 14.81.

What is claimed is:

1. A compound having the Formula I $$X\text{—}C(O)\text{—}Y\text{—}C(O)\text{—}NH\text{—}CH_2\text{—}G\text{—}Im \qquad I$$

wherein

X—C(O)— is D-prolinyl, D-homoprolinyl, R$^m$—(CH$_2$)$_g$—NH—CH$_2$—C(O)—,

T—(CH$_2$)$_a$—C*(R')(Q)—C(O)—,

[structure with benzene ring, (CH$_2$)$_m$, N—B, R', C(O)—]

[structure with benzene ring, (CH$_2$)$_m$, C(O)—, R', N—B]

[structure with cyclohexane ring, (CH$_2$)$_m$, N—B, (CH$_2$)$_n$, R', C(O)—]

[structure with cyclohexane ring, (CH$_2$)$_m$, C(O)—, R', N—B, (CH$_2$)$_n$] or R$^d$—(CH$_2$)$_2$—$\overset{\#}{C}$H(R$^e$)—C(O)—;

in which

R$^d$ is carboxy or methylsulfonyl;

R$^e$ is NHR$^C$, NHCOR$^C$ or NHCOOR$^C$; in which

R$^c$ is (C$_1$–C$_{10}$)alkyl, (C$_3$–C$_8$)cycloalkyl or a (C$_3$–C$_8$) cycloalkyl-(C$_1$–C$_6$)alkyl radical of 4–10 carbons;

T is (C$_3$–C$_8$)cycloalkyl, (C$_1$–C$_8$)alkyl,

[phenyl with Z substituent], or [naphthyl];

a is 0, 1 or 2; and

Q is —OH, (C$_1$–C$_4$)alkoxy, or —NH—A;

A is hydrogen, (C$_1$–C$_4$)alkyl, R"SO$_2$—, R"OC(O)—, R"C(O)—, R"'C(O)— or —(CH$_2$)$_g$—R$^m$;

g is 1, 2, or 3;

B is hydrogen or (C$_1$–C$_4$)alkyl;

R' is hydrogen or (C$_1$–C$_4$)alkyl;

R" is (C$_1$–C$_4$)alkyl, (C$_1$–C$_4$)fluoroalkyl bearing one to five fluoros, —(CH$_2$)$_d$—R$^m$, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

R$^m$ is COOR$^b$, —SO$_2$(C$_1$–C$_4$ alkyl), —SO$_3$H, —P(O)(OR$^b$)$_2$ or tetrazol-5-yl;

R$^n$ is —COOR$^b$ or tetrazol-5-yl;

each R$^b$ is independently hydrogen or (C$_1$–C$_4$)alkyl;

d is 1, 2, or 3;

m is 0, 1, or 2;

n is 0, 1, or 2; and

Z is hydrogen, (C$_1$–C$_4$)alkyl, (C$_1$–C$_4$)alkoxy, hydroxy, halo or (C$_1$–C$_4$)alkylsulfonylamino;

—Y—C(O)— is

—NR$^g$—CH$_2$—C(O)—, [pyrrolidine ring with N, (CH$_2$)$_r$, *C(O)—],

[pyrrolidine ring with N, 4-position R$^p$, *C(O)—], or [bicyclic ring with N, 3a-position, R$^y$, R$^z$, *C(O)—];

in which

R$^g$ is (C$_1$–C$_6$)alkyl, (C$_3$–C$_8$)cycloalkyl, or —(CH$_2$)$_p$—L—(CH$_2$)$_q$—T';

R$^p$ is (C$_1$–C$_6$)alkyl, (C$_3$–C$_8$)cycloalkyl, or —(CH$_2$)$_p$—L—(CH$_2$)$_q$—T';

where p is 0, 1, 2, 3, or 4; L is a bond, —O—, —S—, or —NH—; q is 0, 1, 2 or 3; and T' is (C$_1$–C$_4$)alkyl, (C$_3$–C$_8$) cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

R$^y$ is —CH$_2$—, —O—, —S—, or —NH—; and

R$^z$ is a bond or, when taken with R$^y$ and the three adjoining carbon atoms, forms a saturated carbocyclic ring of 5–8 atoms, one atom of which may be —O—, —S—, or —NH—;

r is 0, 1 or 2;

G is —(CH$_2$)$_s$—, where s is 0, 1, 2, 3, or 4, or G is —(CH$_2$)$_t$—CH=CH—, where t is 0, 1, or 2 and the double bond is trans and is bonded to Im; and Im is an imidazol-4-yl group bearing a radical R at the 5-position in which R is hydrogen, a (C$_1$–C$_4$)alkyl radical which may bear a hydroxy substituent, or a (C₁–C₃)alkoxy-(C₁–C₃)alkyl radical of 2–4 carbons;
or a pharmaceutically acceptable salt thereof;
and further wherein each of the aromatic or heteroaromatic groups listed for the definition of Ar or R″ is independently unsubstituted or substituted with one or two substituents that will afford a stable structure independently selected from halo, hydroxy, (C₁–C₄) alkyl, (C₁–C₄)alkoxy, amino, mono(C₁–C₄ alkyl) amino, di(C₁–C₄ alkyl)amino, —(CH₂)ⱼCOOH, mercapto, —S(O)ₕ(C₁–C₄ alkyl), —NHS(O)ₕ(C₁–C₄ alkyl), —NHC(O) (C₁–C₄ alkyl), —S(O)ₕNH₂, —S(O)ₕNH(C₁–C₄ alkyl), or —S(O)ₕN(C₁–C₄ alkyl)₂, h is 0, 1 or 2, and j is 0, 1, 2, 3, or 4.

2. A compound as claimed in claim 1 in which a (C₁–C₄) alkyl group, a (C₁–C₆)alkyl group, a (C₁–C₈)alkyl group or a (C₁–C₁₀)alkyl group is methyl, ethyl, propyl, isopropyl, butyl, isobutyl or t-butyl; a (C₁–C₄)alkoxy group is methoxy, ethoxy, propoxy or isopropoxy; a (C₃–C₈) cycloalkyl group is cyclopropyl, cyclopentyl or cyclohexyl; a (C₁–C₄)fluoroalkyl group is trifluoromethyl or 2,2,2-trifluoroethyl; aryl is phenyl, naphthyl, furyl, thienyl, pyridyl, indolyl, quinolinyl or isoquinolinyl; and a (C₁–C₃) alkoxy-(C₁–C₃)alkyl radical is methoxymethyl, ethoxymethyl, methoxyethyl or ethoxyethyl.

3. A compound as claimed in claim 1 which is a compound of Formula Ia

Xᵃ—C(O)—Yᵃ—C(O)—NH—CH₂—Gᵃ—Imᵃ     Ia wherein
Xᵃ—C(O)— is D-homoprolinyl,

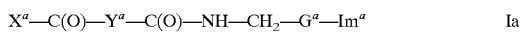

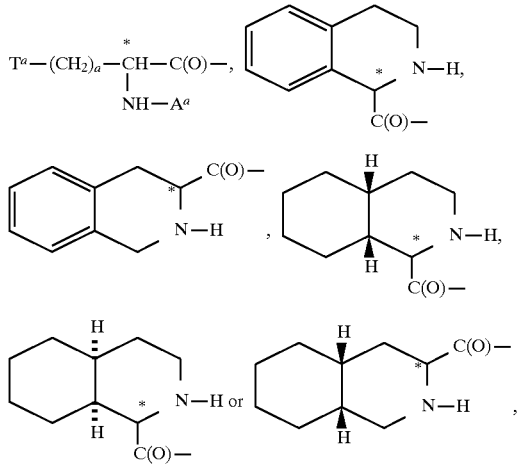

in which Tᵃ is cyclohexyl or phenyl; a is 0, 1, or 2; and Aᵃ is hydrogen, (C₁–C₄)alkyl, (C₁–C₄ alkyl)sulfonyl, (C₁–C₄ alkyl)oxy-carbonyl, (C₁–C₄ alkyl)carbonyl or carboxymethyl;
—Yᵃ—C(O)— is

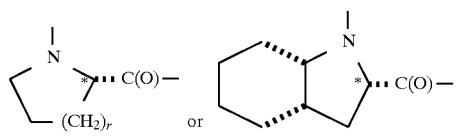

in which r is 0, 1, or 2;
Gᵃ is methylene, ethylene, trimethylene or transvinylidene; and Imᵃ is an imidazol-4-yl group which may bear a methyl or hydroxymethyl substituent at the 5-position;

or a pharmaceutically acceptable salt thereof.

4. A compound as claimed in claim 3 in which

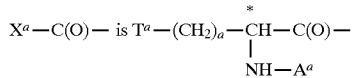

wherein Tᵃ is cyclohexyl or phenyl; a is 1; and Aᵃ is hydrogen, ethylsulfonyl or carboxymethyl;
—Yᵃ—C(O)— is

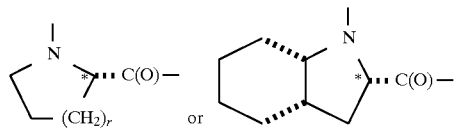

in which r is 0, 1, or 2;
Gᵃ is methylene, ethylene or trans-vinylidene; and Imᵃ is 4-imidazolyl or 5-methylimidazol-4-yl;
or a pharmaceutically acceptable salt thereof.

5. A compound as claimed in claim 4 in which

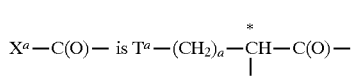

wherein Tᵃ is cyclohexyl; a is 1; and Aᵃ is hydrogen, ethylsulfonyl or carboxymethyl;
—Ya—C(O)— is

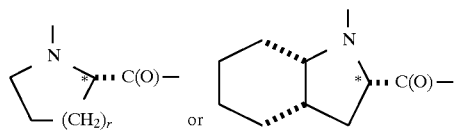

in which r is 1;
Gᵃ is ethylene or trans-vinylidene; and
Imᵃ is 4-imidazolyl;
or a pharmaceutically acceptable salt thereof.

6. A compound as claimed in claim 1 selected from:
a. D-cyclohexylalanyl-N-[(E)-3-(imidazol-4-yl)prop-2-enyl]-L-prolinamide,
b. D-cyclohexylalanyl-N-[3-(imidazol-4-yl)propyl]-L-prolinamide,
c. N-(carboxymethyl)-D-cyclohexylalanyl-N-[(E)-3-(imidazol-4-yl)prop-2-enyl]-L-prolinamide,
d. N-(carboxymethyl)-D-cyclohexylalanyl-N-[3-(imidazol-4-yl)propyl]-L-prolinamide,
e. 1-(D-cyclohexylalanyl)-N-[3-(imidazol-4-yl)propyl]-[2S-(2α,3aβ,7aβ)]-octahydroindol-2-carboxamide, and
f. N-(carboxymethyl)-D-cyclohexylalanyl-N-[2-(imidazol-4-yl)ethyl]-L-prolinamide;
or a pharmaceutically acceptable salt thereof.

7. A compound as claimed in claim 6 selected from:
1. N-(carboxymethyl)-D-cyclohexylalanyl-N-[(E)-3-(imidazol-4-yl)prop-2-enyl]-L-prolinamide, and
2. N-(carboxymethyl)-D-cyclohexylalanyl-N-[3-(imidazol-4-yl)propyl)-L-prolinamide,
or a pharmaceutically acceptable salt thereof.

8. A pharmaceutically acceptable salt of a compound of Formula I as claimed in claim 1 in which X or Y bears an acidic moiety, which salt is made with a base which affords a pharmaceutically acceptable cation, selected from alkalai metal salts, alkaline earth metal salts, aluminum salts, ammonium salts, and salts made from physiologically acceptable organic bases.

9. A pharmaceutical composition comprising a compound of Formula I, or a pharmaceutically acceptable salt thereof, as claimed in claim 1, in association with a pharmaceutically acceptable carrier, diluent or excipient.

10. A process for preparing a compound of Formula I as claimed in claim 1 which comprises:

(A) For a compound of Formula I in which G is —(CH$_2$)$_s$— and s is 2, 3 or 4, hydrogenation of the double bond of a corresponding compound of Formula I in which G is —(CH$_2$)$_t$—CH=CH— and t is 0, 1 or 2;

(B) Coupling an acid of Formula II,

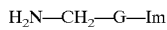     II or an activated derivative thereof, with an amine of Formula III;

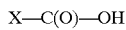     III or (C) Coupling an acid of Formula IV,

X—C(O)—OH     IV or an activated derivative thereof, with an amine of Formula V;

     V whereafter, for any of the above procedures, when a functional group is protected using a protecting group, removing the protecting group;

whereafter, for any of the above procedures, when a pharmaceutically acceptable salt of a compound of Formula I is required, it is obtained by reacting the acidic or basic form of such a compound of Formula I with a base or an acid affording a physiologically acceptable counterion or by any other conventional procedure;

and wherein, unless otherwise specified, the groups X, Y, G and Im and their components have any of the values defined in any of claims 1.

11. A compound of Formula Ip, corresponding to compound of Formula I as claimed in claim 1 in which one or more functional groups is protected,

     Ip which bears one or more of the protecting groups $P^X$, $P^Y$ and $P^I$ wherein $P^X$ is a protecting group(s) for a functional group(s) of X—C(O)—; $P^Y$ is a protecting group(s) for a functional group(s) of —Y—C(O)—; and $P^I$ is a protecting group(s) for a functional group of Im.

12. A compound as claimed in claim 11 wherein the alues for $P^X$, $P^Y$ and $P^I$ are independently selected from the groups which form a t-butylester or benzyl ester when the protected functional group is carboxy, the groups which form a t-butyl urethane or a benzyl urethane when the protected functional group is amino, and the groups which form a methyl ether, t-butyl ether or benzyl ether when the protected functional group is hydroxy; and $p^I$ is the N-tosyl group to protect the imidazole N—H group.

13. A method of inhibiting thrombin comprising administering to a mammal in need of treatment, a thrombin inhibiting dose of a compound of Formula I, or a pharmaceutically acceptable salt thereof, as claimed in claim 1.

* * * * *